United States Patent
Amano et al.

(10) Patent No.: US 9,370,323 B2
(45) Date of Patent: Jun. 21, 2016

(54) CONCENTRATION DETERMINATION APPARATUS, CONCENTRATION DETERMINATION METHOD, AND PROGRAM

(75) Inventors: Kazuhiko Amano, Tokyo-to (JP); Koichi Shimizu, Hokkaido (JP)

(73) Assignees: SEIKO EPSON CORPORATION, Tokyo (JP); NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 919 days.

(21) Appl. No.: 13/274,744

(22) Filed: Oct. 17, 2011

(65) Prior Publication Data
US 2012/0101347 A1     Apr. 26, 2012

(30) Foreign Application Priority Data
Oct. 20, 2010 (JP) ................................ 2010-235927

(51) Int. Cl.
*A61B 5/1455*     (2006.01)
*A61B 5/145*     (2006.01)

(52) U.S. Cl.
CPC ........... *A61B 5/14532* (2013.01); *A61B 5/1455* (2013.01); *A61B 2562/0242* (2013.01)

(58) Field of Classification Search
CPC ..................................................... A61B 5/1455
USPC ................................................... 600/310–344
See application file for complete search history.

(56) References Cited

U.S. PATENT DOCUMENTS 7,239,903 B2 *   7/2007   Eda ............................... 600/310

FOREIGN PATENT DOCUMENTS

| JP | B2-3931638 | 6/2007 |
| JP | B2-3994588 | 10/2007 |

* cited by examiner

*Primary Examiner* — Tse Chen
*Assistant Examiner* — Marjan Fardanesh
(74) *Attorney, Agent, or Firm* — Oliff PLC

(57) ABSTRACT

A concentration determination apparatus may include: an irradiation unit that irradiates short-pulsed light to an observed object; a light receiving unit that receives light backscattered from the observed object; a light intensity acquisition unit that acquires an intensity distribution of the light; an optical path length distribution storage unit that stores a model of an optical path length distribution in each layer of the plurality of layers of the short-pulsed light; an optical path length acquisition unit that acquires the optical path length distribution of each layer; a time-resolved waveform storage unit that stores a model of a time-resolved waveform; a light intensity model acquisition unit that acquires a light intensity model; an integral interval calculation unit that calculates a time range of an area; an optical absorption coefficient calculation and acquisition unit that calculates and acquires an optical absorption coefficient; and a concentration calculation unit that calculates the concentration.

9 Claims, 18 Drawing Sheets

CONCENTRATION DETERMINATION APPARATUS, CONCENTRATION DETERMINATION METHOD, AND PROGRAM

BACKGROUND

1. Technical Field

The present invention relates to a concentration determination apparatus, a probe, a concentration determination method, and a program for non-invasively determining a concentration of a target component in an observed object in any of a plurality of light scattering medium layers in a living body.

This application claims the benefit of priority to Japanese Patent Application No. 2010-235927 filed on Oct. 20, 2010, the contents of which are incorporated herein by reference.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

In recent years, diabetics in an age of gluttony continue to increase each year in Japan. Therefore, diabetics with nephritis also continue to increase each year. Patients suffering from chronic renal insufficiency also continue to increase by ten thousand each year, and currently number over 280 thousand.

Meanwhile, with the advent of an aging society, a demand for preventive medicine and the importance of personal metabolism management are rapidly increasing. In particular, blood sugar value measurement is important. Glucose metabolism in an early stage of diabetes can be evaluated by blood sugar value measurement. The blood sugar value measurement enables early treatment based on early diagnosis of the diabetes.

Traditionally, the blood sugar value measurement is performed by taking a blood sample from a vein of, for example, an arm or a fingertip and measuring enzyme activity for glucose in the blood. This method of measuring a blood sugar value has various problems, such as that taking a blood sample is complicated and painful, and poses a risk of infection. Further, a measurement tip for adhering blood is required. Thereby, there is a need for a non-invasive blood sugar value measurement method that does not require that a blood sample be taken.

As a method of continuously measuring a blood sugar value, equipment for continuously determining glucose corresponding to a blood sugar value in a state in which an injection needle is pushed into a vein has been developed in USA and is currently in clinical trials. However, since the injection needle is pushed into the vein, there are risks of the needle being left or infection during measurement of the blood sugar value.

There is a need for a blood sugar value measurement apparatus capable of frequently measuring a blood sugar value without taking a blood sample and having no risk of infection. Further, there is a need for a miniaturized blood sugar value measurement apparatus capable of being mounted simply and at any time.

Japanese Patent No. 3931638 and Japanese Patent No. 3994588 disclose an apparatus to which the general principle of spectroscopic analysis and measurement is applied using the principle of molecular light absorption as an apparatus for non-invasively measuring a blood sugar level by use of near-infrared continuous light.

This apparatus is intended to prevent an error from occurring in the determination of a biological component concentration under the influence of subcutaneous fat when the biological component concentration is determined by using an infrared spectrum of skin. More specifically, an apparatus irradiates near-infrared continuous light to the skin and calculates a glucose concentration from the light absorption amount.

In this method, a calibration curve representing a relationship among a glucose concentration, a wavelength of irradiated near-infrared light, and a light absorption amount is created in advance. Near-infrared continuous light is irradiated to the skin, and light returned from the skin is scanned in any wavelength band using, for example, a monochromator. A light absorption amount for each wavelength in the wavelength band is obtained, and the light absorption amount in each wavelength is compared with the calibration curve. Accordingly, a glucose concentration, i.e., a blood sugar value, in the blood is calculated.

Skin properties are classified from absorbance at a specific absorption wavelength of subcutaneous fat selected from a wavelength range of 1700 rim to 1800 nm, and a calibration equation is selected as an alternative characteristic of "skin thickness."

Furthermore, a calibration equation is selected after the "skin thickness" is determined to be either equal to or greater than 1.2 mm or less than 1.2 mm by preliminarily estimating the distance between near infrared light receiving and emitting units as 650 μm, and the distance between the light receiving unit and the light emitting unit is selected as either 650 μm or 300 μm.

On the other hand, as biological diagnosis using near-infrared light, for example, a method is known in which absorption amounts of near-infrared light in main components of the skin are measured by biological tissue imaging using a time-resolved measurement method, and each ratio of the main components of the skin, for example, a glucose concentration corresponding to blood sugar, is obtained based on the absorption amounts.

Because the absorption amounts of the main components of the skin depend upon wavelengths, a general method is adopted to estimate the ratios of the main components of the skin by pre-creating a plurality of spectra varying with change factors having the influence on a quantitative determination of the main components of the skin at a plurality of ratios in multivariate analysis, comparing spectra of measurement results of absorption amounts of near-infrared light in the main components of the skin with the plurality of spectra described above, and choosing a consistent spectrum from these spectra.

However, it is not possible to measure only an absorption amount of light of a path passing through a specific depth in an apparatus for non-invasively measuring the blood sugar level by use of near-infrared continuous light in the related art. Therefore, it is not possible to accurately determine a glucose concentration corresponding to blood sugar in the main components of the skin at a specific depth.

The apparatus of Japanese Patent No. 3931638 has the following problems when skin properties are classified from absorbance at a specific absorption wavelength of subcutaneous fat by designating a depth from a skin surface to the subcutaneous fat as the "skin thickness," for example, when the "skin thickness" is used as a substitute for a depth from the skin surface to the subcutaneous fat.

(1) The boundary between a dermis and a subcutaneous tissue of the skin is not uniform as the depth from the surface of the skin.

(2) The dermis has sweat glands for secreting fat and accumulates fat secretions.

(3) When skin properties are classified from absorbance at a specific absorption wavelength of the subcutaneous fat, it is difficult to distinguish the dermis and the subcutaneous fat because fat is included in cells of the dermis and interstitial fluid.

In general, if a biological component concentration is determined using an infrared spectrum of the skin, a depth from a skin surface of an optical path within the skin is generally estimated by a banana-shape characteristic determined by a distance between the light receiving unit and the light emitting unit. For example, the depth from the skin surface of the optical path is estimated to be 325 μm if the distance between the light receiving unit and the light emitting unit is 650 μm, and the depth from the skin surface of the optical path is estimated to be 150 μm if the distance between the light receiving unit and the light emitting unit is 300 μm.

However, in the apparatus of Japanese Patent No. 3931638, it is not possible to specify a portion of which a biological component concentration is determined using an infrared spectrum of the skin for the above-described reason, and therefore it is not possible to selectively measure absorbance in an optical path that passes through a specific portion, wherein stratum reticulare in which glucose is one of interstitial components in the dermis is designated as the specific portion.

SUMMARY

The present invention provides a concentration determination apparatus, a concentration determination method, and a program that can non-invasively and accurately determine the concentration of a target component in a specific layer by selecting an optical absorption coefficient of the specific layer, which is a specific portion in a combination close to an optical path length distribution of a structure of an observed object constituted by a plurality of layers.

The present invention adopts a concentration determination apparatus, a concentration determination method, and a program described below.

A concentration determination apparatus determines a concentration of a target component in a specific layer of an observed object formed of a plurality of layers. The concentration determination apparatus may include: an irradiation unit that irradiates short-pulsed light to the observed object; a light receiving unit that receives light backscattered from the observed object by the irradiation of the short-pulsed light; a light intensity acquisition unit that acquires an intensity distribution of the light from an intensity of the light received by the light receiving unit; an optical path length distribution storage unit that stores a model of an optical path length distribution in each layer of the plurality of layers of the short-pulsed light irradiated to the observed object; an optical path length acquisition unit that acquires the optical path length distribution of each layer of the plurality of layers at a predetermined time of the model of the optical path length distribution; a time-resolved waveform storage unit that stores a model of a time-resolved waveform; a light intensity model acquisition unit that acquires a light intensity model at a predetermined time of the model of the time-resolved waveform; an integral interval calculation unit that calculates a time range of an area corresponding to a light intensity distribution of the specific layer from the intensity distribution of the light based on the intensity distribution of the light, the optical path length distribution, and the light intensity model; an optical absorption coefficient calculation and acquisition unit that calculates and acquires an optical absorption coefficient of the target component in the specific layer by varying the time range for a combination of the intensity distribution of the light and the plurality of layers of the model of the time-resolved waveform acquired by the light intensity model acquisition unit; and a concentration calculation unit that calculates the concentration of the target component in the specific layer based on the optical absorption coefficient of the target component acquired by the optical absorption coefficient calculation and acquisition unit.

In the concentration determination apparatus of the present invention, an irradiation unit irradiates short-pulsed light to an observed object, a light receiving unit receives light backscattered from the observed object by the irradiation of the short-pulsed light, a light intensity acquisition unit acquires an intensity distribution of the light from an intensity of the light received by the light receiving unit, an optical path length acquisition unit acquires an optical path length distribution of each layer of a plurality of layers at a predetermined time of a model of the optical path length distribution, an integral interval calculation unit calculates a time range of an area corresponding to a light intensity distribution of a specific layer from the intensity distribution of the light based on the intensity distribution of the light, the optical path length distribution, and a light intensity model, an optical absorption coefficient calculation and acquisition unit calculates and acquires an optical absorption coefficient of a target component in the specific layer by varying the time range for a combination of the intensity distribution of the light and the plurality of layers of the model of a time-resolved waveform acquired by a light intensity model acquisition unit, and a concentration calculation unit calculates the concentration of a target component in the specific layer based on the optical absorption coefficient of the target component acquired by the optical absorption coefficient calculation and acquisition unit.

As described above, the optical absorption coefficient calculation and acquisition unit calculates the optical absorption coefficient of the target component in the specific layer by varying the time range calculated by the integral interval calculation unit for the combination of the intensity distribution of the light and the plurality of layers of the model of the time-resolved waveform acquired by the light intensity model acquisition unit, thereby selecting the optical absorption coefficient of the specific layer in a combination close to an optical path length distribution of a structure of the observed object. Therefore, it is possible to accurately measure the optical absorption amount of the target component, that is, the concentration of the target component, in the specific layer, and consequently it is possible to non-invasively and accurately determine the concentration of the target component in the specific layer.

The optical absorption coefficient calculation and acquisition unit may include: an optical absorption coefficient calculation unit that calculates an optical absorption coefficient of each layer of the plurality of layers by varying the time range; and an optical absorption coefficient acquisition unit that acquires the optical absorption coefficient of the target component in the specific layer based on the optical absorption coefficient of each layer of the plurality of layers calculated by the optical absorption coefficient calculation unit.

In the concentration determination apparatus of the present invention, an optical absorption coefficient calculation unit calculates an optical absorption coefficient of each layer of the plurality of layers by varying the time range, and an optical absorption coefficient acquisition unit acquires the optical absorption coefficient of the target component in the specific layer based on the optical absorption coefficient of each layer of the plurality of layers calculated by the optical absorption coefficient calculation unit.

Therefore, it is possible to further accurately measure an optical absorption coefficient of the target component, that is, the concentration of the target component, in the specific layer.

The light intensity model acquisition unit may include: a non-absorption light intensity acquisition unit that acquires a non-absorption light intensity model among light intensity models of the short-pulsed light from the time-resolved waveform storage unit; and an absorption light intensity acquisition unit that acquires an absorption light intensity model among the light intensity models of the short-pulsed light.

In the concentration determination apparatus of the present invention, a non-absorption light intensity acquisition unit acquires a non-absorption light intensity model among light intensity models of the short-pulsed light, and an absorption light intensity acquisition unit acquires an absorption light intensity model among the light intensity models of the short-pulsed light. Thereby, it is possible to obtain all light intensity models of the short-pulsed light, and accurately calculate a time range of an area corresponding to a light intensity distribution of the specific layer from the light intensity distribution based on all the light intensity models.

Therefore, it is possible to further accurately measure an optical absorption coefficient of the target component, that is, the concentration of the target component, in the specific layer.

The light intensity acquisition unit may acquire light intensities at a plurality of times $t_1$ to $t_m$ when the number of layers of the observed object within the time range is equal to or greater than n. The optical absorption coefficient calculation unit may calculate an optical absorption coefficient of the specific layer from:

$$\begin{cases} N(t_1)\ln\left(\dfrac{N(t_1)}{I(t_1)}\right) = \sum_{i=1}^{n} \mu_i L_i(t_1) \\ \vdots \\ N(t_m)\ln\left(\dfrac{N(t_m)}{I(t_m)}\right) = \sum_{i=1}^{n} \mu_i L_i(t_m) \end{cases} \quad (1)$$

where $\ln(\bullet)$ denotes a natural logarithm, $I(t)$ denotes a light intensity received by the light receiving unit at a time t within the time range, $N(t)$ denotes a light intensity at the time t within the time range of the model of the time-resolved waveform of the short-pulsed light, $L_i(t)$ denotes an optical path length of an i-th layer at the time t within the time range of the model of the optical path length distribution, and $\mu_i$ denotes an optical absorption coefficient of the i-th layer.

In the concentration determination apparatus of the present invention, the light intensity acquisition unit acquires light intensities at a plurality of times t1 to tm of which the number is equal to or greater than the number of layers, n, of the observed object within the time range, and the optical absorption coefficient calculation unit calculates an optical absorption coefficient of the specific layer from Equation (1).

As described above, it is possible to reduce backscattered light from a layer other than the specific layer as noise by time-resolved measuring the backscattered light, and reduce the influence from a layer other than the specific layer in the concentration of a target component. Therefore, it is possible to further accurately measure the concentration of a target component.

The plurality of times at which the light intensity acquisition unit acquires the light intensities may include a peak time of an optical path length distribution of each layer of the plurality of layers.

In the concentration determination apparatus of the present invention, the plurality of times at which the light intensity acquisition unit acquires the light intensities include a peak time of an optical path length distribution of each layer of the plurality of layers, so that the specific layer can be efficiently selected from a plurality of layers of the observed object. Therefore, it is possible to further accurately measure the concentration of a target component in the specific layer.

The light intensity acquisition unit may acquire light intensities for at least a predetermined time $\tau$ from a predetermined time within the time range. The optical absorption coefficient calculation unit may calculate an optical absorption coefficient of the specific layer from:

$$\begin{cases} \int_0^\tau \ln\left(\dfrac{N(t)}{I(t)}\right) L_1(t)\,dt = \sum_{i=1}^{n} \mu_i \int_0^\tau L_1(t) L_i(t)\,dt \\ \vdots \\ \int_0^\tau \ln\left(\dfrac{N(t)}{I(t)}\right) L_n(t)\,dt = \sum_{i=1}^{n} \mu_i \int_0^\tau L_n(t) L_i(t)\,dt \end{cases} \quad (2)$$

where $\ln(\bullet)$ denotes a natural logarithm, $I(t)$ denotes a light intensity received by the light receiving unit at a time t within the time range, $N(t)$ denotes a light intensity at the time t within the time range of the model of the time-resolved waveform of the short-pulsed light, $L_i(t)$ denotes an optical path length of an i-th layer at the time t within the time range of the model of the optical path length distribution, n denotes the number of layers of the observed object, and $\mu_i$ denotes an optical absorption coefficient of the i-th layer.

In the concentration determination apparatus of the present invention, the light intensity acquisition unit acquires light intensities for at least a predetermined time $\tau$ from a predetermined time within the time range, and the optical absorption coefficient calculation unit calculates an optical absorption coefficient of the specific layer from Equation (2).

As described above, it is possible to reduce backscattered light from a layer other than the specific layer as noise by time-resolved measuring the backscattered light, and reduce the influence from a layer other than the specific layer in the concentration of a target component. Therefore, it is possible to further accurately measure the concentration of a target component.

The irradiation unit may irradiate light of a plurality of wavelengths 1 to q. The optical absorption coefficient calculation unit may calculate the optical absorption coefficient in the specific layer for each of the plurality of wavelengths irradiated by the irradiation unit. The concentration calculation unit may calculate the concentration of the target component in the specific layer from:

$$\begin{cases} \mu_{a(1)} - \mu_{a(2)} = \sum_{j=1}^{p} g_j(\varepsilon_{j(1)} - \varepsilon_{j(2)}) \\ \vdots \\ \mu_{a(q-1)} - \mu_{a(q)} = \sum_{j=1}^{p} g_j(\varepsilon_{j(q-1)} - \varepsilon_{j(q)}) \end{cases} \quad (3)$$

where $\mu_{a(i)}$ denotes an optical absorption coefficient of a wavelength i in an a-th layer, which is the specific layer, $g_j$ denotes a molar concentration of a j-th component forming the observed object, $\epsilon_{j(i)}$ denotes an optical absorption coefficient of the wavelength i of the j-th component, p denotes the number of main components forming the observed object, and q denotes the number of types of wavelengths irradiated by the irradiation unit.

In the concentration determination apparatus of the present invention, the irradiation unit irradiates light of a plurality of wavelengths 1 to q, the optical absorption coefficient calculation unit calculates the optical absorption coefficient in the specific layer for each of the plurality of wavelengths irradiated by the irradiation unit, and the concentration calculation unit calculates the concentration of the target component in the specific layer from Equation (3).

As described above, it is possible to reduce backscattered light from a layer other than the specific layer as noise by time-resolved measuring the backscattered light, and reduce the influence from a layer other than the specific layer in the concentration of a target component. Therefore, it is possible to further accurately measure the concentration of a target component.

A plurality of pieces of light irradiated by the irradiation unit may include light of a wavelength at which the optical absorption coefficient of the target component becomes large.

A plurality of pieces of light irradiated by the irradiation unit may include light of a wavelength at which orthogonality of an absorption spectrum distribution of each component of main components constituting the observed object becomes high.

A concentration determination method may use a concentration determination apparatus for determining a concentration of a target component in a specific layer of an observed object, wherein the concentration determination apparatus includes an optical path length distribution storage unit for storing a model of an optical path length distribution in each layer of a plurality of layers from short-pulsed light irradiated to the observed object formed of the plurality of layers and a time-resolved waveform storage unit for storing a model of a time-resolved waveform of the short-pulsed light irradiated to the observed object. The concentration determination method may include: irradiating, by an irradiation unit, the short-pulsed light to the observed object; receiving, by a light receiving unit, light backscattered from the observed object by the irradiation of the short-pulsed light; acquiring, by a light intensity acquisition unit, an intensity of the light received by the light receiving unit; acquiring, by an optical path length acquisition unit, the optical path length distribution of each layer of the plurality of layers at a predetermined time of the model of the optical path length distribution from the optical path length distribution storage unit; acquiring, by a light intensity model acquisition unit, a light intensity model at the predetermined time of the model of the time-resolved waveform of the short-pulsed light from the time-resolved waveform storage unit; calculating, by an integral interval calculation unit, a time range of an area corresponding to a light intensity distribution of the specific layer from the intensity distribution of the light based on the intensity distribution of the light, the optical path length distribution of each layer of the plurality of layers acquired by the optical path length acquisition unit, and the light intensity model acquired by the light intensity model acquisition unit; calculating and acquiring, by an optical absorption coefficient calculation and acquisition unit, an optical absorption coefficient of the target component in the specific layer by varying the time range calculated by the integral interval calculation unit for a combination of the intensity distribution of the light acquired by the light intensity acquisition unit and a plurality of models of the time-resolved waveform acquired by the light intensity model acquisition unit; and calculating, by a concentration calculation unit, the concentration of the target component in the specific layer based on the optical absorption coefficient of the target component acquired by the optical absorption coefficient calculation and acquisition unit.

In the concentration determination method of the present invention, an irradiation unit irradiates short-pulsed light to an observed object, a light receiving unit receives light backscattered from the observed object by the irradiation of the short-pulsed light, a light intensity acquisition unit acquires an intensity distribution of the light from an intensity of the light received by the light receiving unit, an optical path length acquisition unit acquires an optical path length distribution of each layer of the plurality of layers at a predetermined time of a model of the optical path length distribution, an integral interval calculation unit calculates a time range of an area corresponding to a light intensity distribution of a specific layer from the intensity distribution of the light based on the intensity distribution of the light, the optical path length distribution, and a light intensity model, an optical absorption coefficient calculation and acquisition unit calculates and acquires the optical absorption coefficient of a target component in the specific layer by varying the time range for a combination of the intensity distribution of the light and the plurality of layers of the model of a time-resolved waveform acquired by a light intensity model acquisition unit, and a concentration calculation unit calculates the concentration of the target component in the specific layer based on the optical absorption coefficient of the target component acquired by the optical absorption coefficient calculation and acquisition unit.

As described above, the optical absorption coefficient calculation and acquisition unit calculates and acquires the optical absorption coefficient of the target component in the specific layer by varying the time range for the combination of the intensity distribution of the light and the plurality of layers of the model of the time-resolved waveform acquired by the light intensity model acquisition unit, thereby selecting the optical absorption coefficient of the specific layer in a combination close to an optical path length distribution of a structure of the observed object. Therefore, it is possible to accurately measure the optical absorption amount of the target component, that is, the concentration of the target component, in the specific layer, and consequently it is possible to non-invasively and accurately determine the concentration of the target component in the specific layer.

A program may cause a computer of a concentration determination apparatus for determining a concentration of a target component in a specific layer of an observed object, wherein the apparatus includes an optical path length distribution storage unit for storing a model of an optical path length distribution in each layer of a plurality of layers from short-pulsed light irradiated to the observed object formed of the plurality of layers and a time-resolved waveform storage unit for storing a model of a time-resolved waveform of the short-pulsed light irradiated to the observed object, to execute: an irradiation procedure of irradiating the short-pulsed light to the observed object; a light receiving procedure of receiving light backscattered from the observed object by the irradiation of the short-pulsed light; a light intensity acquisition procedure of acquiring an intensity of the light received in the light receiving procedure; an optical path length acquisition procedure of acquiring the optical path length distribution of each layer of the plurality of layers at a predetermined time of the model of the optical path length distribution from the optical path length distribution storage unit; a light intensity model acquisition procedure of acquiring a light intensity model at the predetermined time of the model of the time-resolved waveform of the short-pulsed light from the time-resolved waveform storage unit; an integral interval calculation procedure of calculating a time range of an area corresponding to a light intensity distribution of the specific layer from the intensity distribution of the light based on the intensity distribution of the light acquired in the light intensity acquisition procedure, the optical path length distribution of each layer of the plurality of layers acquired in the optical path length acquisition procedure, and the light intensity model acquired in the light intensity model acquisition procedure; an optical absorption coefficient calculation and acquisition procedure of calculating and acquiring an optical absorption coefficient of the target component in the specific layer by varying the time range calculated in the integral interval calculation procedure for a combination of the intensity distribution of the light acquired in the light intensity acquisition procedure and a plurality of models of the time-resolved waveform acquired in the light intensity model acquisition procedure; and a concentration calculation procedure of calculating the concentration of the target component in the specific layer based on the optical absorption coefficient of the target component acquired in the optical absorption coefficient calculation and acquisition procedure.

In the program of the present invention, after an irradiation procedure of irradiating the short-pulsed light to the observed object, a light receiving procedure of receiving light backscattered from the observed object by the irradiation of the short-pulsed light, and a light intensity acquisition procedure of acquiring the intensity of the light received in the light receiving procedure are executed, the program sequentially executes an integral interval calculation procedure of calculating a time range of an area corresponding to a light intensity distribution of the specific layer from the intensity distribution of the light based on the intensity distribution of the light acquired in the light intensity acquisition procedure, the optical path length distribution of each layer of the plurality of layers acquired in an optical path length acquisition procedure, and the light intensity model acquired in a light intensity model acquisition procedure, an optical absorption coefficient calculation and acquisition procedure of calculating and acquiring an optical absorption coefficient of the target component in the specific layer by varying the time range calculated in the integral interval calculation procedure for a combination of the intensity distribution of the light acquired in the light intensity acquisition procedure and a plurality of models of the time-resolved waveform acquired in the light intensity model acquisition procedure, and a concentration calculation procedure of calculating the concentration of the target component in the specific layer based on the optical absorption coefficient of the target component acquired in the optical absorption coefficient calculation and acquisition procedure.

As described above, the program sequentially executes the integral interval calculation procedure of calculating the time range of the area corresponding to the light intensity distribution of the specific layer from the intensity distribution of the light based on the intensity distribution of the light acquired in the light intensity acquisition procedure, the optical path length distribution of each layer of the plurality of layers acquired in the optical path length acquisition procedure, and the light intensity model acquired in the light intensity model acquisition procedure and the optical absorption coefficient calculation and acquisition procedure of calculating and acquiring the optical absorption coefficient of the target component in the specific layer by varying the time range calculated in the integral interval calculation procedure for the combination of the intensity distribution of the light acquired in the light intensity acquisition procedure and the plurality of models of the time-resolved waveform acquired in the light intensity model acquisition procedure, thereby selecting an optical absorption coefficient of the specific layer in a combination close to an optical path length distribution of a structure of the observed object. Therefore, it is possible to accurately measure the optical absorption amount of the target component, that is, the concentration of a target component, in the specific layer, and consequently it is possible to non-invasively and accurately determine the concentration of the target component in the specific layer.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE PREFERRED EMBODIMENTS

A concentration determination apparatus, a concentration determination method and a program in accordance with preferred embodiments of the present invention will be described.

In the present invention, a description will be given in which a blood sugar value measurement apparatus is used as a concentration determination apparatus, skin of a person's palm is used as an observed object, glucose is used as a target component, and short pulsed light having a specific wavelength is used as light having a specific wavelength.

First Embodiment

Figure 1:
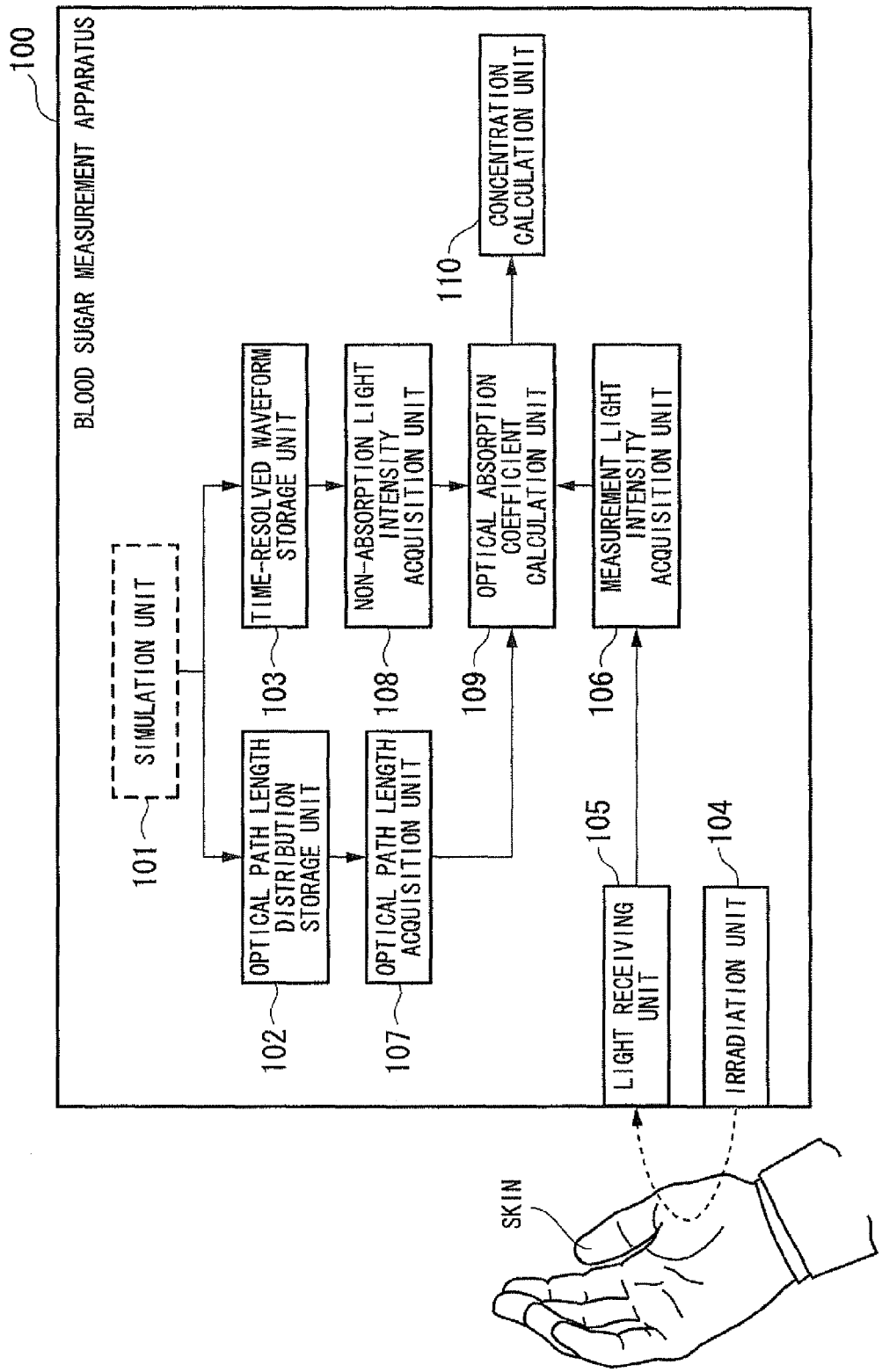
FIG. 1 is a schematic block diagram showing a configuration of a blood sugar value measurement apparatus in accordance with a first embodiment of the present invention.

FIG. 1 is a schematic block diagram showing a configuration of a blood sugar value measurement apparatus 100 in accordance with a first embodiment of the present invention. A blood sugar measurement apparatus 100 includes a simulation unit 101, an optical path length distribution storage unit 102, a time-resolved waveform storage unit 103, an irradiation unit 104, a light receiving unit 105, a measurement light intensity acquisition unit 106, an optical path length acquisition unit 107, a non-absorption light intensity acquisition unit (a light intensity model acquisition unit) 108, an optical absorption coefficient calculation unit 109, and a concentration calculation unit 110.

The blood sugar measurement apparatus 100 measures a concentration of glucose (a target component) included in a dermis (a specific layer) of skin (an observed object).

The simulation unit 101 performs a simulation by irradiating light to a skin model having an optical absorption coefficient of 0.

The optical path length distribution storage unit 102 stores an optical path length distribution of the skin model having an optical absorption coefficient of 0.

The time-resolved waveform storage unit 103 stores a time-resolved waveform of the skin model having an optical absorption coefficient of 0.

The irradiation unit 104 irradiates short-pulsed light to the skin. A plurality of pieces of short-pulsed light irradiated by the irradiation unit 104 include light of a wavelength at which orthogonality of an absorption spectrum distribution of each component of main components constituting the skin becomes high, that is, light of a wavelength at which a maximum value of an absorption spectrum of a specific component in a certain main component among the main components constituting the skin is largely different from maximum values of absorption spectra of other components, The light receiving unit 105 receives light backscattered by the skin from short-pulsed light.

Here, the short-pulsed light has a time of a pulse width that is shorter than a time when light is directly propagated from the irradiation unit 104 to the light receiving unit 105 in air, and, for example, is pulse light in which a half-value width of the pulse light is 0.1 ps to 10 ps and a time interval between two pieces of pulse light is 1 ps to 100 ps.

The optical path length distribution is expressed as a distribution function in which a length of a moving path of light (photons) (an optical path length) is based on a time until the light (photons) arrives at the light receiving unit 105.

The measurement light intensity acquisition unit 106 acquires a light intensity of light received by the light receiving unit 105 at a certain time.

The optical path length acquisition unit 107 acquires an optical path length at a certain time from the optical path length distribution storage unit 102.

The non-absorption light intensity acquisition unit 108 acquires a light intensity model from the time-resolved waveform storage unit 103 when an optical absorption coefficient is zero (0) at a certain time.

The optical absorption coefficient calculation unit 109 calculates an optical absorption coefficient in the dermis of the skin to which short-pulsed light is irradiated. The concentration calculation unit 110 calculates a concentration of glucose included in the dermis.

In the blood sugar measurement apparatus 100, the irradiation unit 104 irradiates the short-pulsed light to the skin, and the light receiving unit 105 receives light backscattered by the skin from the short-pulsed light.

Here, a structure of human skin tissue, which is an observed object, will be described.

Figure 2:
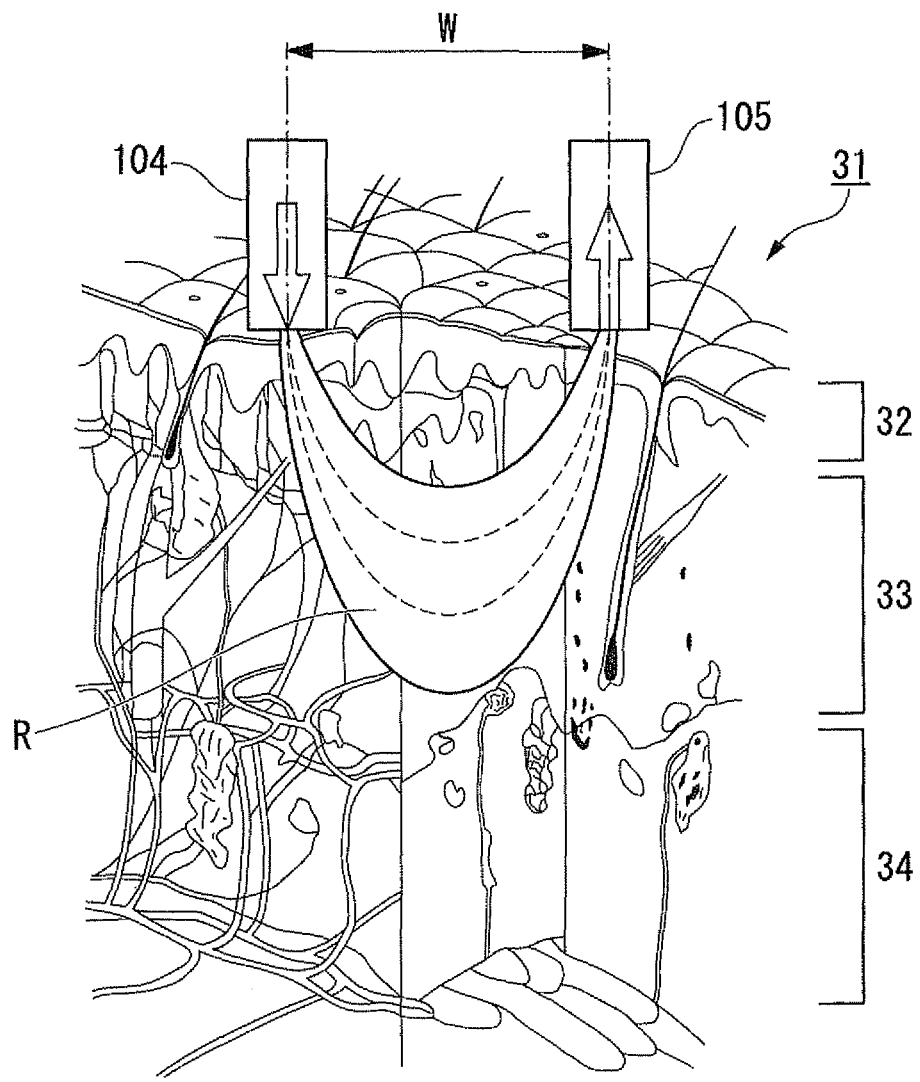
FIG. 2 is a schematic diagram showing a cross section of a human skin tissue.

FIG. 2 is a schematic diagram showing a cross section of the human skin tissue. Skin 31 includes three layers of an epidermis 32, a dermis (a specific layer) 33, and subcutaneous tissue 34.

The epidermis 32 is a layer generally containing about 60% water, protein, lipid and glucose in a thin layer having an outermost thickness of 0.2 mm to 0.3 mm, and includes a stratum corneum, a stratum granulosum, a stratum spinosum, a bottom layer, and the like.

The dermis 33 is a layer generally containing about 60% water, protein, lipid and glucose in a layer formed under the epidermis 32 and having a thickness of 0.5 mm to 2 mm. The dermis 33 internally includes nerves, hair roots, sebaceous glands, sweat glands, hair follicles, blood vessels, lymph vessels, and the like.

In a layer having a thickness of 1 to 3 mm formed under the dermis 33, the majority of the subcutaneous tissue 34 generally includes 90% or more lipid, and the remainder is subcutaneous fat including water.

Within the dermis 33, capillaries and the like are developed, a mass transfer corresponding to glucose in the blood rapidly occurs, and the concentration of glucose in the dermis 33 may also vary with the glucose concentration (a blood sugar level) in the blood. In the blood sugar measurement apparatus 100, the irradiation unit 104 and the light receiving unit 105 are in close contact with the surface of the skin 31 at a predetermined input-output distance W, and light is irradiated from the irradiation unit 104 to the surface of the skin 31 in the close contact state. The light is reflected by tissue within the skin 31, and the reflected light is scattered towards the irradiation unit 104 and the light receiving unit 105, so that the scattered light (backscattered light) is detected by the light receiving unit 105.

Next, the measurement light intensity acquisition unit 106 acquires an intensity of light received by the light receiving unit 105 at a time t. Next, the optical path length acquisition unit 107 acquires the optical path length of each layer of the skin at the time t in a propagation light path length distribution of a skin model from the optical path length distribution storage unit 102, and the non-absorption light intensity acquisition unit 108 acquires the intensity of light at the time t in a time-resolved waveform of short-pulsed light in the skin model from the time-resolved waveform storage unit 103.

Next, the optical absorption coefficient calculation unit 109 calculates an optical absorption coefficient of the dermis of the skin based on the light intensity acquired by the measurement light intensity acquisition unit 106, the optical path length of each layer of the skin acquired by the optical path length acquisition unit 107, and the light intensity acquired by the non-absorption light intensity acquisition unit 108, and the concentration calculation unit 110 calculates a concentration of glucose in the dermis based on the optical absorption coefficient calculated by the optical absorption coefficient calculation unit 109.

Because the glucose concentration is calculated using the optical absorption coefficient of the dermis 33, which is a layer of a specific depth of the skin 31, the blood sugar measurement apparatus 100 can reduce the influence of noise due to a layer other than the dermis 33, and calculate a concentration of glucose included in the dermis 33, which is the layer of the specific depth. Therefore, it is possible to non-invasively and accurately measure an optical absorption amount of glucose included in the layer of the specific depth, that is, the concentration of glucose.

Next, an operation of the blood sugar measurement apparatus 100 will be described.

Before a blood sugar level is measured, the blood sugar measurement apparatus 100 needs to pre-calculate an optical path length distribution and a time-resolved waveform in each layer of the skin model.

First, a method of calculating the optical path length distribution and the time-resolved waveform of the skin model will be described.

Initially, the simulation unit 101 generates the skin model. The skin model is generated by deciding a light scattering coefficient, an optical absorption coefficient, and a thickness of each layer of the skin. Here, if a portion of the skin is specified, it is preferable that a scattering coefficient and a thickness of each layer in the specified skin portion be decided by pre-taking samples because an individual difference is small. The thickness of the epidermis 32 is about 0.3 mm, the thickness of the dermis 33 is about 1.2 mm, and the thickness of the subcutaneous tissue 34 is about 3.0 mm.

The optical absorption coefficient of the skin model used here is assumed to be zero. This is because an optical absorption amount is calculated using the skin model.

When the skin model is generated, the simulation unit 101 performs a simulation by irradiating light to the skin model. At this time, it is necessary to decide a distance W between a position of the irradiation unit 104 and a position of the light receiving unit 105. The simulation is performed, for example, using a Monte-Carlo method.

The simulation based on the Monte-Carlo method is performed, for example, as follows.

First, the simulation unit 101 performs a calculation operation by irradiating photons to the skin model by designating a model of irradiated light as photons (a light flux). The photons irradiated to the skin model move within the skin model. At this time, a distance L, which is a distance until the photons move to the next point, and a direction θ are decided by a random number R. The simulation unit 101 calculates the distance L until the photons move to the next point by Equation (4).

$$L = ln(R/\mu_s) \quad (4)$$

Here, ln(A) is a natural logarithm of A, and $\mu_s$ is a scattering coefficient of an s-th layer (one of the epidermis, the dermis, and the subcutaneous tissue) of the skin model.

The simulation unit 101 calculates the direction θ until the photons move to the next point by Equation (5).

$$\theta = \cos^{-1}\left[\frac{1}{2g}\left\{1 + g^2 - \left(\frac{1-g^2}{1+g-2gR}\right)^2\right\}\right] \quad (5)$$

Here, g is an anisotropy parameter, which is an average of a cosine (cos) of a scattering angle. The anisotropy parameter of the skin is about 0.9.

The simulation unit 101 iterates the calculation using the above-described

Equations (4) and (5) every unit time, thereby calculating a moving path of photons from the irradiation unit 104 to the light receiving unit 105. The simulation unit 101 calculates a moving distance for a plurality of photons. For example, the simulation unit 101 calculates a moving distance for 108 photons.

Figure 3:
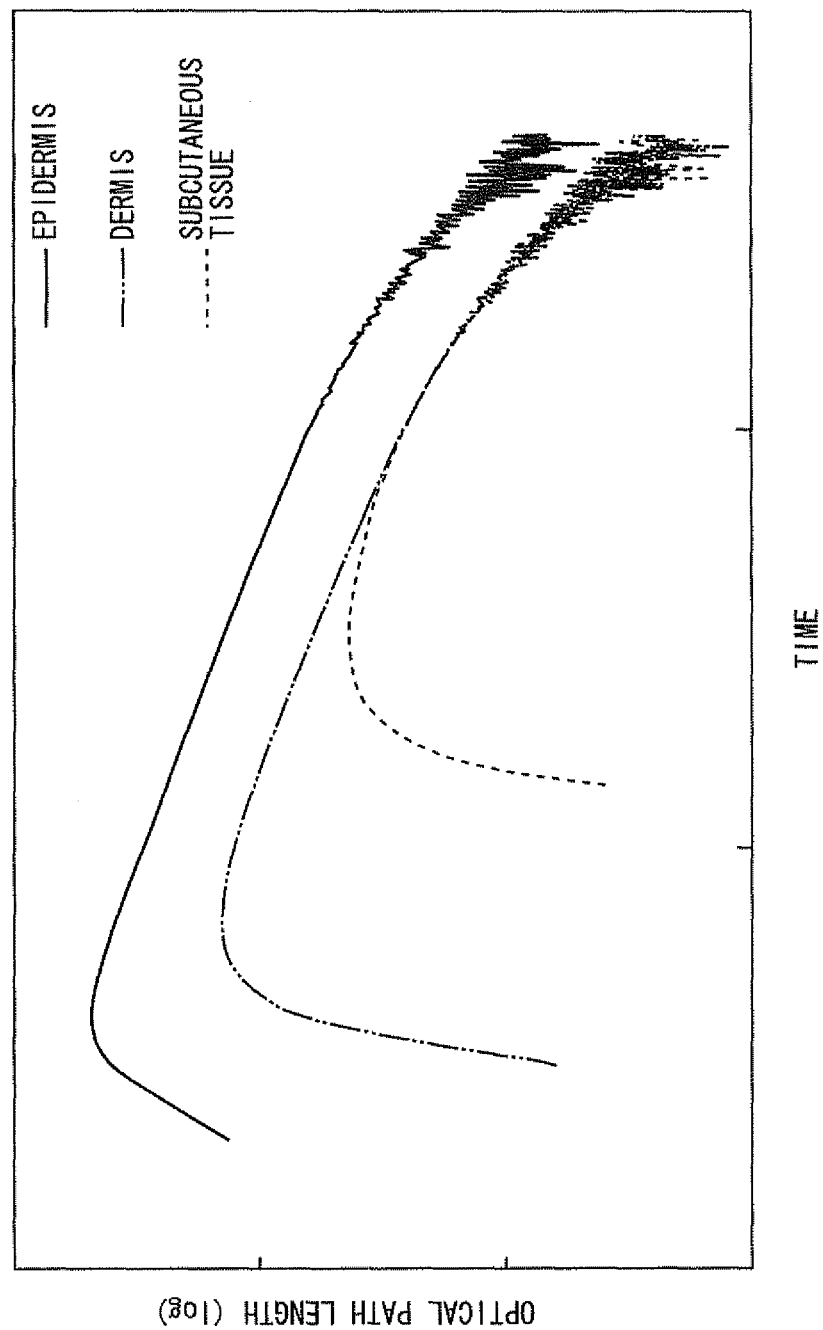
FIG. 3 is a diagram showing an optical path length distribution of each layer calculated by a simulation unit.

FIG. 3 is a diagram showing an optical path length distribution of each layer calculated by the simulation unit 101.

In FIG. 3, the horizontal axis represents an elapsed time from photon irradiation, and the vertical axis represents an optical path length (log).

The simulation unit 101 classifies a moving path of each photon arriving at the light receiving unit 105 according to each layer through which the moving path passes. The simulation unit 101 calculates an average length of the moving path of the photons arriving every unit time for each classified layer, thereby calculating the optical path length distribution of each layer of the skin as shown in FIG. 3.

Figure 4:
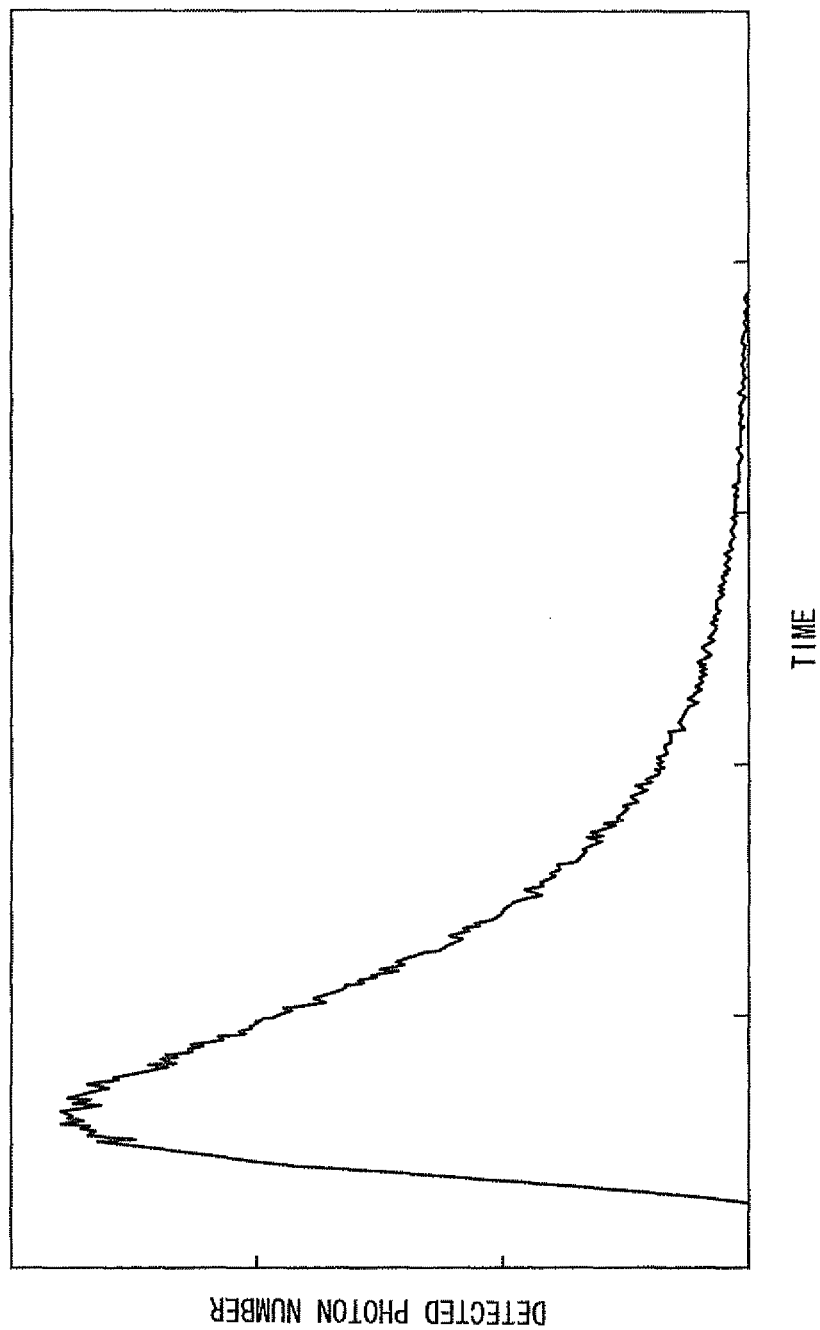
FIG. 4 is a diagram showing a time-resolved waveform calculated by the simulation unit.

Also, the simulation unit 101 calculates the number of photons arriving at the light receiving unit 104 every unit time, thereby calculating a time-resolved waveform of the skin model as shown in FIG. 4.

FIG. 4 is a diagram showing the time-resolved waveform calculated by the simulation unit 101. In FIG. 4, the horizontal axis represents an elapsed time from photon irradiation, and the vertical axis represents the number of photons detected by the light receiving unit 105.

According to the above-described process, the simulation unit 101 calculates optical path length distributions and time-resolved waveforms of the skin model for a plurality of wavelengths. At this time, it is preferable that the simulation unit 101 calculate an optical path length distribution and a time-resolved waveform for light of a wavelength at which orthogonality between absorption spectra of main components (water, protein, lipid, glucose, and the like) of the skin becomes high, that is, for light of a wavelength at which a maximum value of an absorption spectrum of a specific component in a certain main component among the main components (water, protein, lipid, glucose, and the like) of the skin is largely different from maximum values of absorption spectra of other components.

Figure 5:
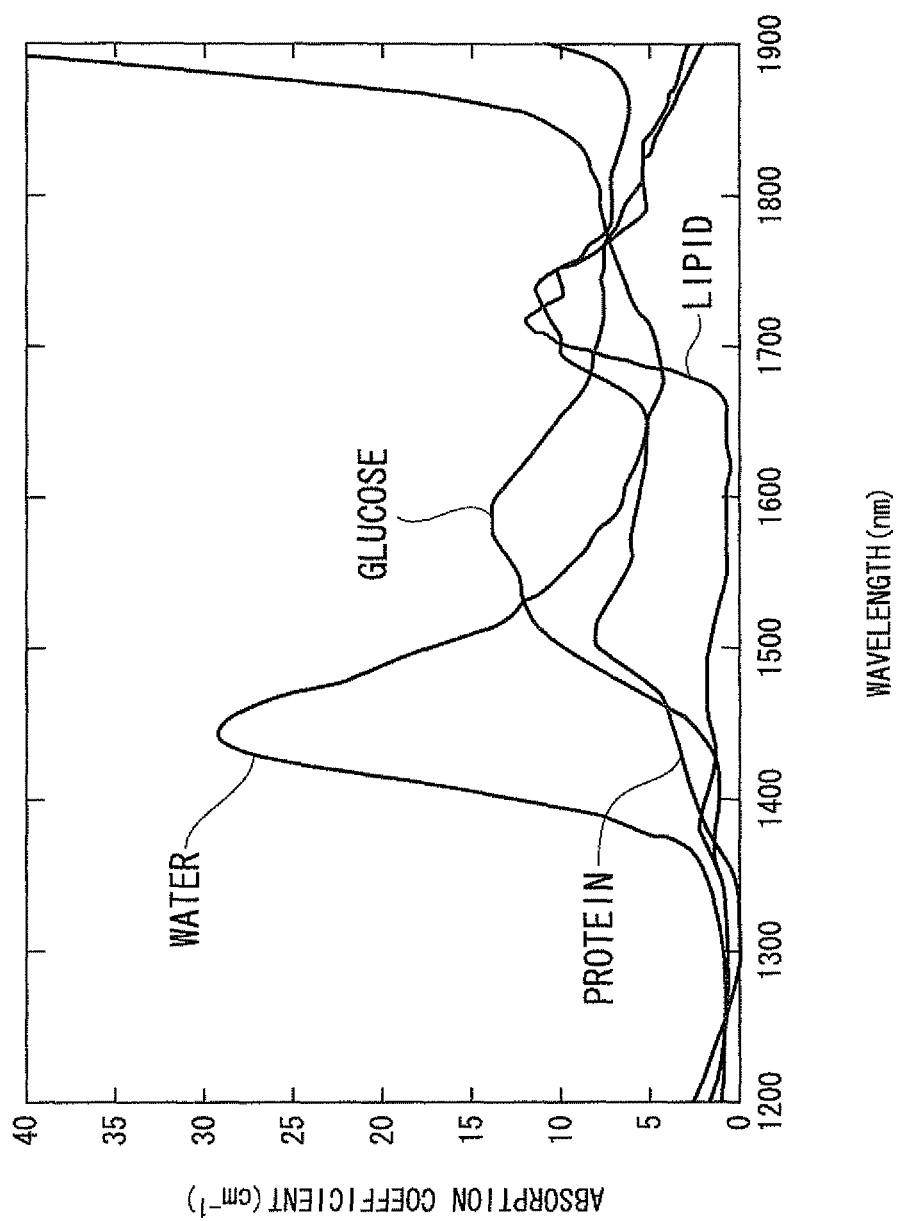
FIG. 5 is a graph showing absorption spectra of main components of the skin.

FIG. 5 is a graph showing absorption spectra of the main components of the skin. In FIG. 5, the horizontal axis represents an irradiated light wavelength, and the vertical axis represents an absorption coefficient.

According to FIG. 5, it can be seen that the absorption coefficient of glucose is maximum when the wavelength is 1600 nm and the absorption coefficient of water is maximum when the wavelength is 1450 nm.

Thus, it is preferable that the simulation unit 101 calculate an optical path length distribution and a time-resolved waveform for light of a wavelength, for example, such as 1450 nm or 1600 nm, at which an absorption spectrum distribution of each component of the main components constituting the skin becomes high, that is, for light of a wavelength at which a maximum value of an absorption spectrum of a specific component in a certain main component among the main components constituting the skin is largely different from maximum values of absorption spectra of other components.

When the simulation unit 101 calculates optical path length distributions and time-resolved waveforms of the skin model for a plurality of wavelengths, the optical path length distribution storage unit 102 stores information on the calculated optical path length distributions, and the time-resolved waveform storage unit 103 stores information on the calculated time-resolved waveforms. The simulation unit 101 may not be included in the blood sugar measurement apparatus 100. In this case, the blood sugar measurement apparatus 100 measures a blood sugar level by storing results of a simulation performed by an external apparatus in the optical path length distribution storage unit 102 and the time-resolved waveform storage unit 103.

Figure 6:
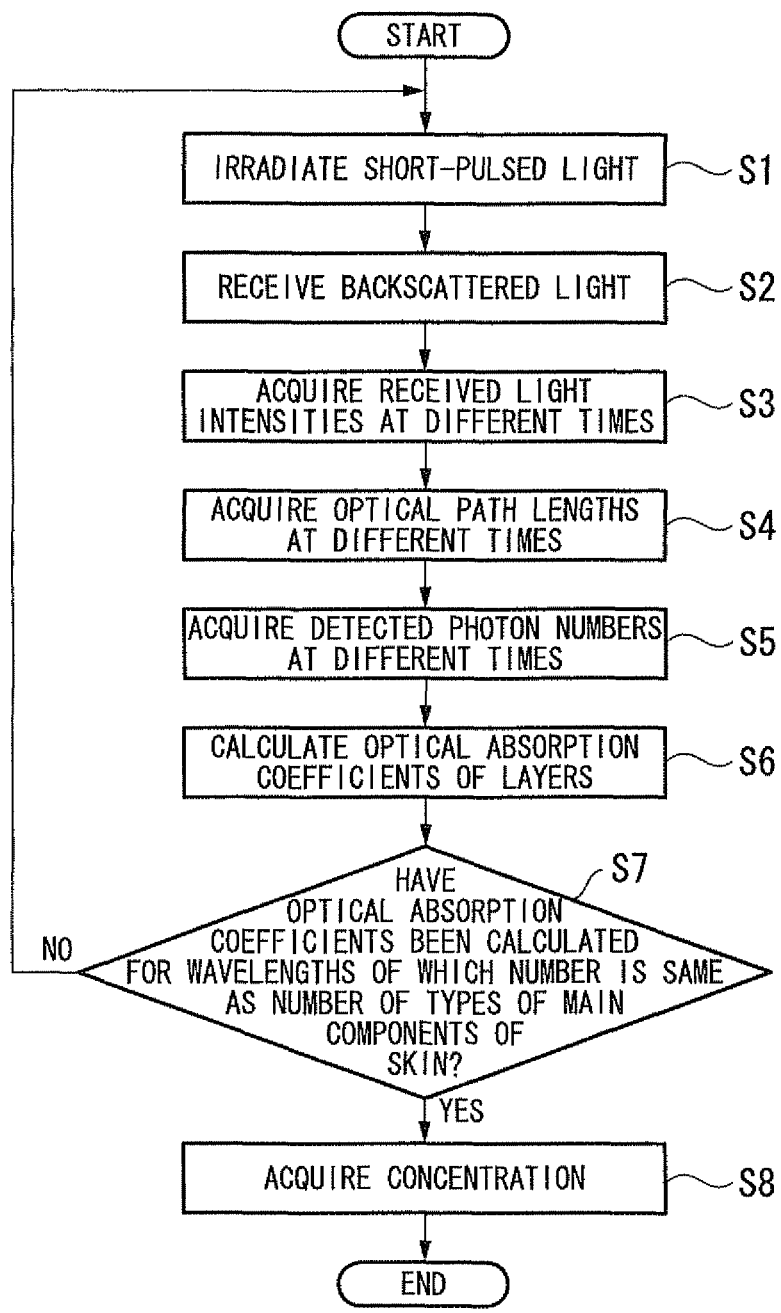
FIG. 6 is a flowchart showing a process of measuring a blood sugar value by the blood sugar value measurement apparatus in accordance with the first embodiment of the present invention.

Next, an operation in which the blood sugar measurement apparatus 100 measures a blood sugar level will be described based on FIG. 6. FIG. 6 is a flowchart showing a process of measuring a blood sugar value by the blood sugar value measurement apparatus in accordance with the first embodiment of the present invention.

First, when a user (a person to be measured) applies the blood sugar measurement apparatus 100 to skin such as on a wrist and operates the blood sugar measurement apparatus 100 by pressing a measurement start switch (not shown) or the like, the irradiation unit 104 irradiates short-pulsed light of a wavelength $\lambda_1$ to the skin 31 (step S1).

Here, the wavelength $\lambda_1$ is one of a plurality of wavelengths for which the simulation unit 101 calculates optical path length distributions and time-resolved waveforms.

For example, it is preferable that an optical path length distribution and a time-resolved waveform be calculated for light of a wavelength at which an optical absorption coefficient of a specific component in a certain main component among the main components constituting the skin becomes greater than optical absorption coefficients of other components, that is, for light of a wavelength at which a minimum value of the optical absorption coefficient of the specific component is largely different from those of the other components.

When the irradiation unit 104 irradiates short-pulsed light, the light receiving unit 105 receives light backscattered by the skin 31 after irradiation from the irradiation unit 104 (step S2).

At this time, the light receiving unit 105 stores a received light intensity in an internal memory (not shown) every unit time (for example, every 1 picosecond) from the initiation of irradiation.

Then, when the light receiving unit 105 completes light reception, the measurement light intensity acquisition unit 106 acquires received light intensities I(t) of which the number is the same as the number of layers of the skin at different times t stored in the internal memory (step S3).

In a flowchart of FIG. 6, the case in which concentration measurement is performed using four types of wavelengths in three layers of the skin will be described.

That is, when the concentration measurement is performed using the four types of wavelengths in the three layers of the skin, the measurement light intensity acquisition unit 106 acquires received light intensities $I(t_1)$ to $I(t_3)$ at three different times $t_1$ to $t_3$. The received light intensities of which the number is the same as the number of layers of the skin are acquired because the absorption coefficient of each layer of the skin is calculated by simultaneous equations in a process to be described later.

It is preferable that the times $t_1$ to $t_3$ at which the measurement light intensity acquisition unit 106 acquires the light intensities be those at which propagation light path length distributions of the layers of the skin peak. That is, it is preferable that each light intensity be acquired at a time obtained by adding a time at which the optical path length of each layer of the skin is maximized in the graph shown in FIG. 3 to a time at which the irradiation unit 104 irradiates short-pulsed light.

When the measurement light intensity acquisition unit 106 acquires the received light intensities $I(t_1)$ to $I(t_3)$, the optical path length acquisition unit 107 acquires optical path lengths $L_1(t_1)$ to $L_1(t_3)$, $L_2(t_1)$ to $L_2(t_3)$, and $L_3(t_1)$ to $L_3(t_3)$ of the layers of the skin at the times $t_1$ to $t_3$ from an optical path length distribution of the wavelength $\lambda_1$ stored in the optical path length distribution storage unit 102 (step S4).

When the measurement light intensity acquisition unit 106 acquires the received light intensities $I(t_1)$ to $I(t_3)$, the non-absorption light intensity acquisition unit 108 acquires detected photon numbers $N(t_1)$ to $N(t_3)$ at the times $t_1$ to $t_3$ from a time-resolved waveform of the wavelength $\lambda_1$ stored by the time-resolved waveform storage unit 103 (step S5).

When the optical path length acquisition unit 107 acquires the optical path lengths of the layers of the skin and the non-absorption light intensity acquisition unit 108 acquires the detected photon numbers, the optical absorption coefficient calculating unit 109 calculates optical absorption coefficients $\mu_1$ to $\mu_3$ of the layers of the skin based on Equations (6) (step S6). Here, the optical absorption coefficient $\mu_1$ indicates the optical absorption coefficient of the epidermis, the optical absorption coefficient $\mu_2$ indicates the optical absorption coefficient of the dermis, and the optical absorption coefficient $\mu_3$ indicates the optical absorption coefficient of the subcutaneous tissue.

$$\begin{cases} N'(t_1)\ln\left(\dfrac{N'(t_1)}{I'(t_1)}\right) = \sum_{i=1}^{3} \mu_i L_i(t_1) \\ N'(t_2)\ln\left(\dfrac{N'(t_2)}{I'(t_2)}\right) = \sum_{i=1}^{3} \mu_i L_i(t_2) \\ N'(t_3)\ln\left(\dfrac{N'(t_3)}{I'(t_3)}\right) = \sum_{i=1}^{3} \mu_i L_i(t_3) \end{cases} \quad (6)$$

where $N'(t) = \dfrac{N(t)}{N_{in}}$ and $I'(t) = \dfrac{I(t)}{I_{in}}$

Here, ln(A) denotes a natural logarithm of A, and N(t) denotes a light intensity at the time t of a model of a time-resolved waveform of short-pulsed light of a specific wavelength $\lambda_k$. $I_{in}$ denotes the light intensity of the short-pulsed light irradiated by the irradiation unit 104. $N_{in}$ denotes the number of photons according to irradiation in a simulation performed by the simulation unit 101.

When the optical absorption coefficient calculating unit 109 calculates the optical absorption coefficients $\mu_1$ to $\mu_3$ of the layers of the skin, the optical absorption coefficient calculation unit 109 determines whether or not the optical absorption coefficients $\mu_1$ to $\mu_3$ have been calculated for wavelengths of which the number is the same as the number of types of main components of the skin (step S7).

In this embodiment, because a blood sugar level is measured by designating the main components of the skin as four types of water, protein, lipid, and glucose, the optical absorption coefficient calculation unit 109 determines whether or not the optical absorption coefficients $\mu_1$ to $\mu_3$ for four types of wavelengths $\lambda_1$ to $\lambda_4$ have been calculated. Here, the wavelengths $\lambda_1$ to $\lambda_4$ are selected from among a plurality of wavelengths for which the simulation unit 101 has calculated optical path length distributions and time-resolved waveforms.

If the optical absorption coefficient calculation unit 109 determines that the optical absorption coefficients $\mu_1$ to $\mu_3$ have not been calculated for the wavelengths $\lambda_1$ to $\lambda_4$ (step S7: NO), the process returns to step S1 to calculate the optical absorption coefficients $\mu_1$ to $\mu_3$ of the wavelengths $\lambda_1$ to $\lambda_4$ for which the optical absorption coefficients $\rho_1$ to $\mu_3$ have not been calculated.

On the other hand, if the optical absorption coefficient calculation unit 109 determines that the optical absorption coefficients $\mu_1$ to $\mu_3$ of the wavelengths $\lambda_1$ to $\lambda_4$ have been calculated (step S7: YES), the concentration calculation unit 110 calculates the concentration of glucose included in the dermis based on Equations (7) (step S8).

$$\begin{cases} \mu_{2(1)} - \mu_{2(2)} = \sum_{i=1}^{4} g_i(\varepsilon_{i(1)} - \varepsilon_{i(2)}) \\ \vdots \\ \mu_{2(4)} - \mu_{2(1)} = \sum_{i=1}^{4} g_i(\varepsilon_{i(4)} - \varepsilon_{i(1)}) \end{cases} \quad (7)$$

Here, $\mu_{2(1)}$ to $\mu_{2(4)}$ denote optical absorption coefficients of the wavelengths $\lambda_1$ to $\lambda_4$ in the dermis. $g_1$ to $g_4$ denote molar concentrations of water, protein, lipid and glucose, which are the main components of the skin in the dermis. $\varepsilon_{1(1)}$ to $\varepsilon_{1(4)}$ denote molar extinction coefficients of water for the wavelengths $\lambda_1$ to $\lambda_4$. $\varepsilon_{2(1)}$ to $\varepsilon_{2(4)}$ denote molar extinction coefficients of protein for the wavelengths $\lambda_1$ to $\lambda_4$. $\varepsilon_{3(1)}$ to $\varepsilon_{3(4)}$ denote molar extinction coefficients of lipid for the wavelengths $\lambda_1$ to $\lambda_4$. $\varepsilon_{4(1)}$ to $\varepsilon_{4(4)}$ denote molar extinction coefficients of glucose for the wavelengths $\lambda_1$ to $\lambda_4$.

That is, the molar concentration of glucose included in the dermis can be acquired by calculating g4 of Equations (7).

Here, the reason it is possible to obtain a molar concentration of glucose by Equations (7) will be described.

Because the wavelength dependence of the scattering coefficient of the skin is small, it is possible to neglect a variation to a wavelength of a detected photon number N(t) and an optical path length Ln(t). According to the Beer-Lambert law, (Absorbance=Molar Extinction Coefficient×Molar Concentration) can be expressed. Thereby, it is possible to derive Equations (7) indicating a relationship between an absorption coefficient difference obtained in the dermis and a molar extinction coefficient of each component forming the skin by deleting the detected photon number N(t) from time-resolved measurements obtained at two wavelengths.

According to this embodiment, short-pulsed light is irradiated and a concentration of glucose is determined based on an intensity of light received at a predetermined time. Thereby, the absorption coefficient of the dermis can be selectively calculated from the light received at the predetermined time. Thereby, it is possible to calculate the concentration of glucose in a specific layer of the skin, reduce the influence of noise due to other layers, and calculate the blood sugar level with high accuracy.

Second Embodiment

The second embodiment of the present invention will be described in detail. A configuration of a blood sugar measurement apparatus according to the second embodiment is the same as that of the blood sugar measurement apparatus 100 according to the first embodiment, and operations of the measurement light intensity acquisition unit 106, the optical path length acquisition unit 107, the non-absorption light intensity acquisition unit 108, and the optical absorption coefficient calculation unit 109 are different.

Figure 7:
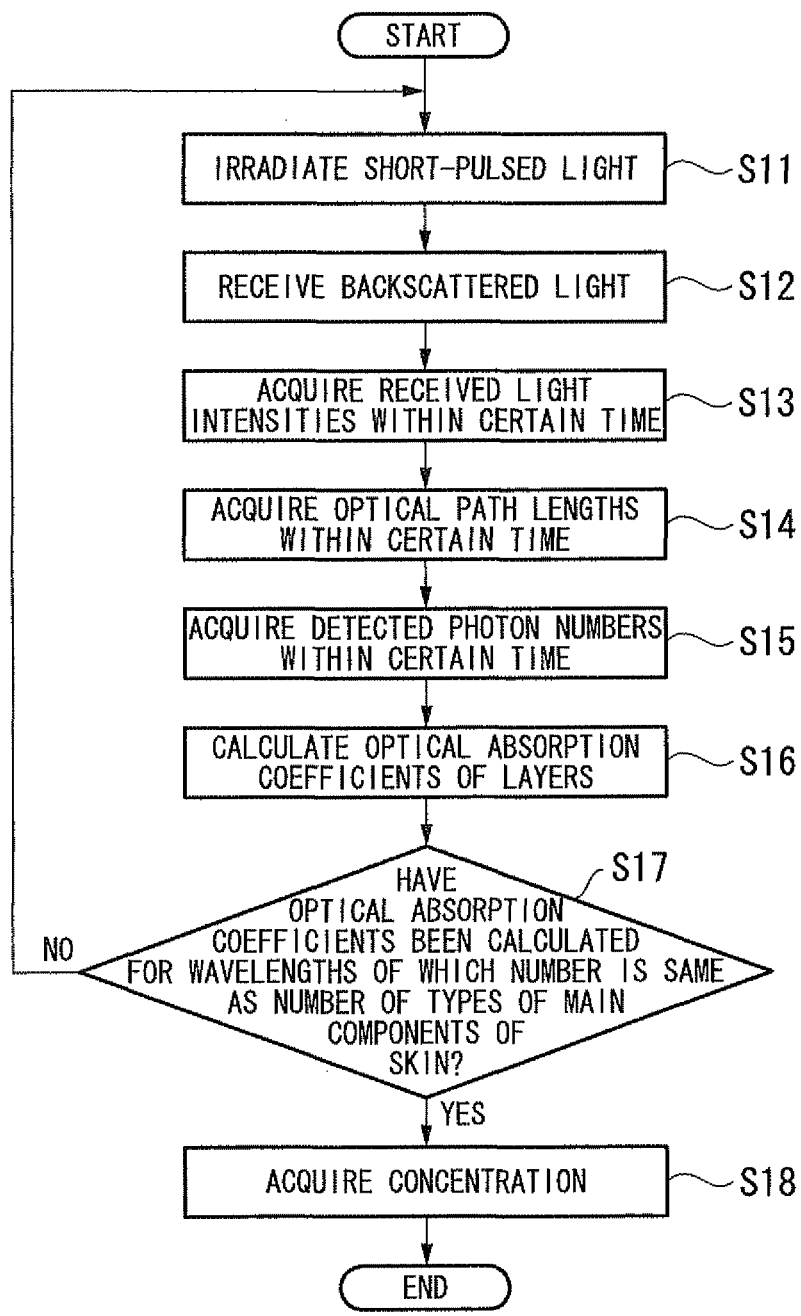
FIG. 7 is a flowchart showing a process of measuring a blood sugar value by the blood sugar value measurement apparatus in accordance with a second embodiment of the present invention.

FIG. 7 is a flowchart showing an operation in which the blood sugar measurement apparatus measures the blood sugar level.

First, when the blood sugar measurement apparatus 100 is operated, an irradiation unit 104 irradiates short-pulsed light of a wavelength $\lambda_1$ to the skin (step S11). Here, the wavelength $\lambda_1$ is one of a plurality of wavelengths for which the simulation unit 101 calculates optical path length distributions and time-resolved waveforms.

When the irradiation unit 104 irradiates short-pulsed light, the light receiving unit 105 receives light backscattered by the skin after irradiation from the irradiation unit 104 (step S12). At this time, the light receiving unit 105 stores a received light intensity in an internal memory (not shown) every unit time (for example, every 1 picosecond) from the initiation of irradiation.

When the light receiving unit 105 completes light reception, the measurement light intensity acquisition unit 106 acquires a time distribution of received light intensities for a time τ after a certain time from received light intensities stored in the internal memory (step S13).

When the measurement light intensity acquisition unit 106 acquires the time distribution of the received light intensities for the time τ, the optical path length acquisition unit 107 acquires an optical path length of each layer of the skin for the time τ after a certain time from an optical path length distribution of the wavelength $\lambda_1$ stored by the optical path length distribution storage unit 102.

In a flowchart of FIG. 7, the case where concentration measurement is performed using four types of wavelengths for three layers of the skin will be described.

That is, if the concentration measurement is performed using the four types of wavelengths for the three layers of the skin, the measurement light intensity acquisition unit 106 acquires optical path lengths $L_1$ to $L_3$ of the layers of the skin for the time τ after the certain time (step S14).

Also, when the measurement light intensity acquisition unit 106 acquires the time distribution of the received light intensities, the non-absorption light intensity acquisition unit 108 acquires detected photon numbers for the time τ after the certain time from the time-resolved waveform of the wavelength $\lambda_1$ stored by the time-resolved waveform storage unit 103 (step S15).

When the optical path length acquisition unit 107 acquires an optical path length of each layer of the skin and the non-absorption light intensity acquisition unit 108 acquires a detected photon number, the optical absorption coefficient calculation unit 109 calculates optical absorption coefficients $\mu_1$ to $\mu_3$ of the layers of the skin based on Equations (8) (step S16). Here, the optical absorption coefficient $\mu_1$ indicates an optical absorption coefficient of the epidermis. The optical absorption coefficient $\mu_2$ indicates an optical absorption coefficient of the dermis. The optical absorption coefficient $\mu_3$ indicates the optical absorption coefficient of the subcutaneous tissue.

$$\begin{cases} \int_0^\tau \ln\left(\frac{N'(t)}{I'(t)}\right) L_1(t) dt = \sum_{i=1}^{3} \mu_i \int_0^\tau L_1(t) L_i(t) dt \\ \int_0^\tau \ln\left(\frac{N'(t)}{I'(t)}\right) L_2(t) dt = \sum_{i=1}^{3} \mu_i \int_0^\tau L_2(t) L_i(t) dt \\ \int_0^\tau \ln\left(\frac{N'(t)}{I'(t)}\right) L_3(t) dt = \sum_{i=1}^{3} \mu_i \int_0^\tau L_3(t) L_i(t) dt \end{cases} \quad (8)$$

$$\text{where } N'(t) = \frac{N(t)}{N_{in}} \text{ and } I'(t) = \frac{I(t)}{I_{in}}$$

Here, ln(A) denotes a natural logarithm of A. I(t) denotes a received light intensity of the light receiving unit 105 at a time t, and $I_{in}$ denotes a light intensity of the short-pulsed light irradiated by the irradiation unit 104. N(t) denotes a detected photon number at the time t of a time-resolved waveform, and $N_{in}$ is the number of photons according to irradiation in a simulation performed by the simulation unit 101. $L_1(t)$ to $L_3(t)$ denote optical path lengths of the layers of the skin at the time t.

When the optical absorption coefficient calculating unit 109 calculates the optical absorption coefficients $\mu_1$ to $\mu_3$ of the layers of the skin, the optical absorption coefficient calculation unit 109 determines whether or not the optical absorption coefficients $\mu_1$ to $\mu_3$ have been calculated for wavelengths of which the number is the same as the number of types of main components of the skin (step S17). In this embodiment, because a blood sugar level is measured by designating the main components of the skin as four types of water, protein, lipid, and glucose, the optical absorption coefficient calculation unit 109 determines whether or not the optical absorption coefficients $\mu_1$ to $\mu_3$ for four types of wavelengths $\lambda_1$ to $\lambda_4$ have been calculated. Here, the wavelengths $\lambda_1$ to $\lambda_4$ are selected from among a plurality of wavelengths for which the simulation unit 101 has calculated optical path length distributions and time-resolved waveforms.

Here, if the optical absorption coefficient calculation unit 109 determines that the optical absorption coefficients $\mu_1$ to $\mu_3$ have not been calculated for the wavelengths $\lambda_1$ to $\lambda_4$ (step S17: NO), the process returns to step S11 to calculate the optical absorption coefficients $\mu_1$ to $\mu_3$ of the wavelengths $\lambda_1$ to $\lambda_4$ for which the optical absorption coefficients $\mu_1$ to $\mu_3$ have not been calculated.

On the other hand, if the optical absorption coefficient calculation unit 109 determines that the optical absorption coefficients $\mu_1$ to $\mu_3$ of the wavelengths $\lambda_1$ to $\lambda_4$ have been calculated (step S17: YES), the concentration calculation unit 110 calculates a concentration of glucose included in the dermis based on the above-described Equations (7) (step S18).

According to this embodiment, the absorption coefficients $\mu_1$ to $\mu_3$ are calculated by an integration value of the optical path lengths for the time τ. Thereby, it is possible to reduce the influence on calculation results of the absorption coefficients $\mu_1$ to $\mu_3$ due to an error included in measured light intensities I(t).

While the first and second embodiments have been described with reference to the drawings, the specific configurations are not limited thereto. Various design changes and the like may be made without departing from the scope of the invention.

For example, although the case where the concentration determination method is implemented in the blood sugar measurement apparatus 100, and the blood sugar measurement apparatus 100 measures the concentration of glucose included in the dermis of the skin has been described in the first and second embodiments, the concentration determination method is not limited thereto, and may be used in other apparatuses that determine the concentration of a target component in a specific layer of an observed object formed of a plurality of layers.

Although the blood sugar measurement apparatus 100 is configured to include the simulation unit 101, the optical path length distribution storage unit 102, and the time-resolved waveform storage unit 103 in the first and second embodiments, it is not necessary to separately provide the simulation unit 101 if simulation results of the simulation unit 101 are stored in the optical path length distribution storage unit 102 and the time-resolved waveform storage unit 103.

The blood sugar measurement apparatus 100 may internally include a computer system. Operations of the processing units described above or operations of some of the processing units may be stored in a computer-readable recording medium in the form of a program. The above-described process is performed by the computer reading and executing the program. Here, the computer-readable recording medium may be a magnetic disk, a magneto-optical disc, a compact disc read-only memory (CD-ROM), a digital versatile disc-read only memory (DVD-ROM), a semiconductor memory, or the like. The computer program may be distributed to the computer through a communication line, and the computer receiving the distribution may execute the program.

The above-described program may be used to implement a part of the above-described function.

In addition, the program may be a differential file (differential program) capable of implementing the above-described function in combination with a program already recorded in the computer system.

Third Embodiment

Figure 8:
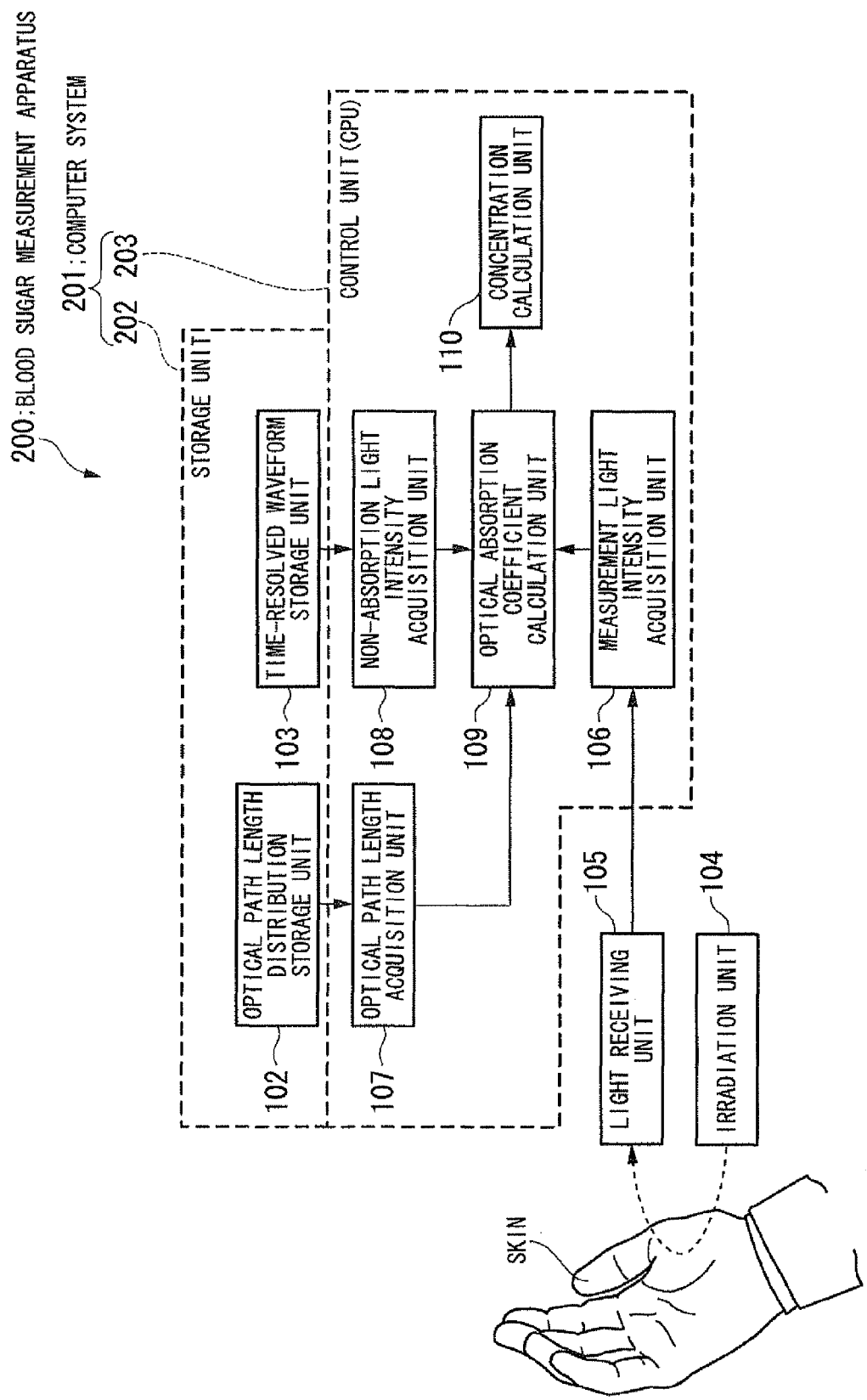
FIG. 8 is a schematic block diagram showing a configuration of a blood sugar measurement apparatus in accordance with a third embodiment of the present invention.

FIG. 8 is a schematic block diagram showing a configuration of a blood sugar measurement apparatus in accordance with a third embodiment of the present invention.

A difference of the blood sugar measurement apparatus 200 of this embodiment from the blood sugar measurement apparatus 100 of the first embodiment is that the blood sugar measurement apparatus 200 includes the irradiation unit 104, the light receiving unit 105, and a computer system 201, wherein the computer system 201 includes a storage unit 202 and a control unit (a central processing unit (CPU)) 203, the storage unit 202 executes functions of the optical path length distribution storage unit 102 and the time-resolved waveform storage unit 103 storing simulation results of the simulation unit 101, and the control unit (CPU) 203 executes functions of the measurement light intensity acquisition unit 106, the optical path length acquisition unit 107, the non-absorption light intensity acquisition unit 108, the optical absorption coefficient calculation unit 109, and the concentration calculation unit 110.

The blood sugar measurement apparatus 200 of this embodiment can also have the same function and effect as the blood sugar measurement apparatus 100 of the first embodiment.

Fourth Embodiment

Figure 9:
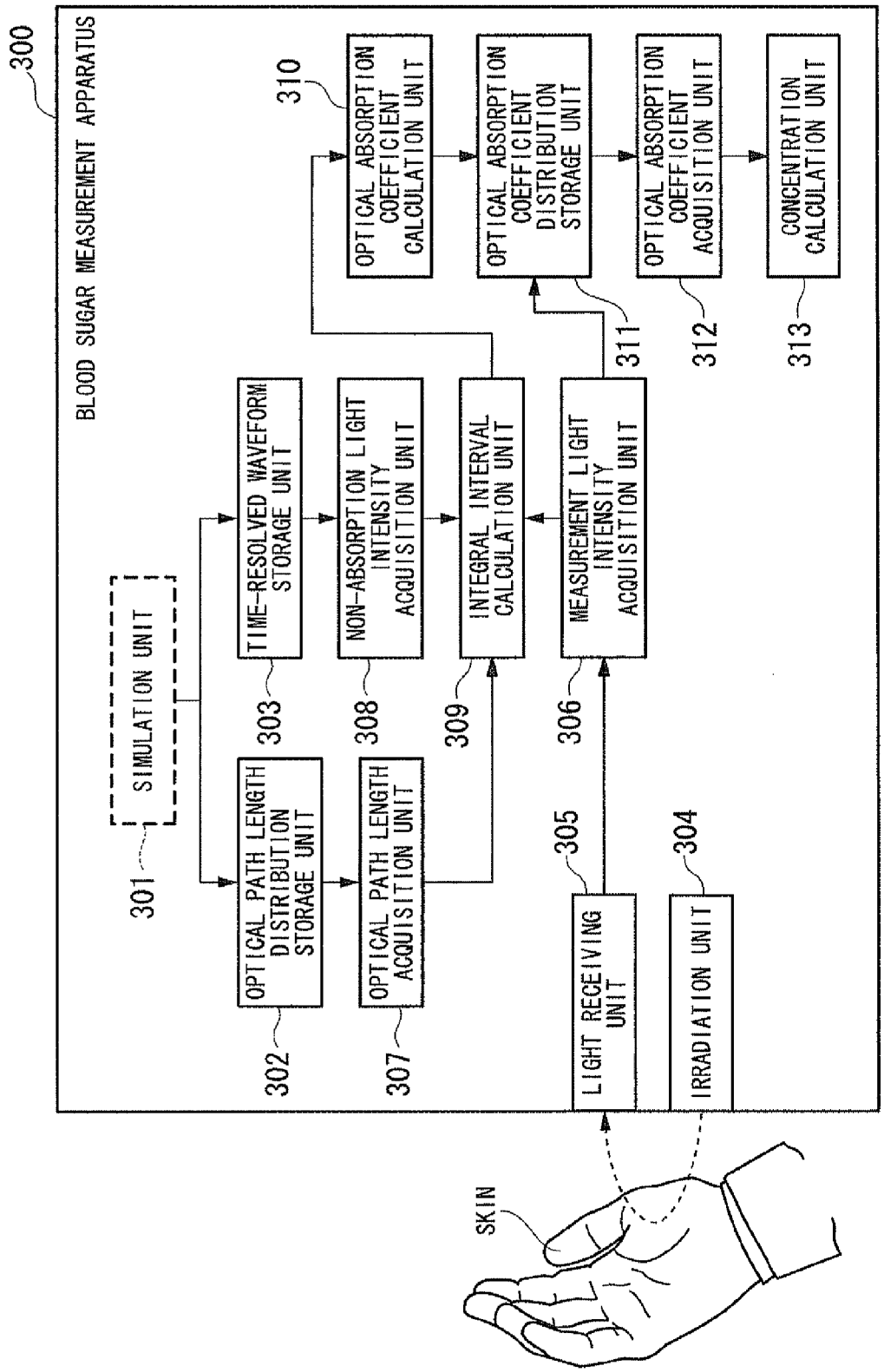
FIG. 9 is a schematic block diagram showing a configuration of a blood sugar measurement apparatus in accordance with a fourth embodiment of the present invention.

FIG. 9 is a schematic block diagram showing a configuration of a blood sugar measurement apparatus in accordance with a fourth embodiment of the present invention.

A blood sugar measurement apparatus 300 non-invasively determines a concentration of glucose (a target component) included in a dermis (a specific layer) among a plurality of layers constituting skin (an observed object) such as on a palm, and includes a simulation unit 301, an optical path length distribution storage unit 302, a time-resolved waveform storage unit 303, an irradiation unit 304, a light receiving unit 305, a measurement light intensity acquisition unit 306, an optical path length acquisition unit 307, a non-absorption light intensity acquisition unit (a light intensity model acquisition unit) 308, an integral interval calculation unit 309, an optical absorption coefficient calculation unit 310, an optical absorption coefficient distribution storage unit 311, an optical absorption coefficient acquisition unit 312, and a concentration calculation unit 313.

The simulation unit 301 performs a simulation by irradiating light to a skin model having an optical absorption coefficient of 0.

The optical path length distribution storage unit 302 stores a model of an optical path length distribution in each layer constituting the skin according to short-pulsed light irradiated to the skin. Here, an optical path length distribution of the skin model having the optical absorption coefficient of 0 is stored.

Here, the short-pulsed light has a time of a pulse width that is shorter than a time when light is directly propagated from the irradiation unit 304 to the light receiving unit 305 in air, and, for example, is pulse light in which a half-value width of the pulse light is 0.1 ps to 10 ps and a time interval between two pieces of pulse light is 1 ps to 100 ps.

The optical path length distribution is expressed as a distribution function in which a length of a moving path of light (photons) (an optical path length) based on a time until the light (photons) arrives at the light receiving unit 305.

The time-resolved waveform storage unit 303 stores a model of a time-resolved waveform of short-pulsed light irradiated to the skin. Herein, a time-resolved waveform of the skin model having an optical absorption coefficient of 0 is stored. Here, the time-resolved waveform of the short-pulsed light is expressed as a distribution function in which an intensity of light (photons) received by the light receiving unit 305 is based on an elapsed time from the time of irradiation of the short-pulsed light.

It is not necessary to separately provide the simulation unit 301 if simulation results of the simulation unit 301 are stored in the optical path length distribution storage unit 302 and the time-resolved waveform storage unit 303.

The irradiation unit 304 irradiates short-pulsed light to the skin. The light is scattered by tissue within the skin, and diffused into the skin. Part of the diffused light arrives at the light receiving unit 305 (as backscattered light). A path in which the backscattered light arriving at the light receiving unit 305 is propagated into the skin becomes a banana-shaped path as shown in FIG. 2. A plurality of pieces of short-pulsed light irradiated by the irradiation unit 304 include light of a wavelength at which orthogonality of an absorption spectrum distribution of each component of main components constituting the skin becomes high, that is, light of a wavelength at which a maximum value of an absorption spectrum of a specific component in a certain main component among the main components constituting the skin is largely different from maximum values of absorption spectra of other components.

The light receiving unit 305 receives light backscattered by the skin from the short-pulsed light. The light receiving unit 305 includes an internal memory (not shown) storing a received light intensity. The internal memory may be replaced with an external memory electrically connected to the light receiving unit 305.

The measurement light intensity acquisition unit 306 acquires a light intensity at a certain time from light received by the light receiving unit 305.

The optical path length acquisition unit 307 acquires an optical path length of each layer of the skin at a predetermined time of a model of an optical path length distribution from the optical path length distribution storage unit 302. Here, the optical path length is acquired from the optical path length distribution storage unit 302 at a certain time. Here, the optical path length is the length of a path of light until the short-pulsed light irradiated from the irradiation unit 304 penetrates the skin, is scattered into the skin and is detected by the light receiving unit 305. As will be described later, the optical path length of each layer of the skin is estimated by determining the distance between the irradiation unit 304 and the light receiving unit 305.

The non-absorption light intensity acquisition unit 308 acquires a light intensity model when an optical absorption coefficient is zero (0) at a predetermined time of a model of a time-resolved waveform of the short-pulsed light (upon non-absorption) from the time-resolved waveform storage unit 303. Here, a non-absorption light intensity is acquired from the time-resolved waveform storage unit 303 at a certain time.

The integral interval calculation unit 309 calculates an integral interval, which is a time range (a time width) of an area corresponding to a light intensity of each layer of the skin from a light intensity distribution, based on the light intensity distribution acquired by the measurement light intensity acquisition unit 306, an optical path length distribution acquired by the optical path length acquisition unit 307, and a non-absorption light intensity acquired by the non-absorption light intensity acquisition unit 308.

Here, the integral interval is a time width of an area corresponding to a light intensity of a specific layer in the light intensity distribution, and can be decided by a start time, an end time, and an increment time.

For example, the start time, the end time, and the increment time of the integral interval are decided using (1) a time from when a light intensity output by the light receiving unit 305 receiving backscattered light is detected at more than minimum detection sensitivity of the measurement light intensity acquisition unit 306 to when a light intensity equal to the minimum detection sensitivity is detected, (2) a time characteristic of a non-absorption light intensity acquired from the time-resolved waveform storage unit 303 storing the non-absorption light intensity obtained by the simulation unit 301, (3) the distance between the light receiving unit 305 and the irradiation unit 304 in contact with a skin surface, and (4) the size and optical characteristics (such as a scattering coefficient, an absorption coefficient, an anisotropy parameter, or a refractive index) of a skin model provided to the simulation unit 301.

The optical absorption coefficient calculation unit 310 calculates an optical absorption coefficient of glucose (a target component) in the dermis (a specific layer) by varying an integral interval, which is a time range (a time width) of an area corresponding to a light intensity of the dermis (a specific layer).

Here, an optical absorption coefficient and an estimation error rate of each layer of the skin 31 within the integral interval defined by the integral interval calculation unit 309 are obtained and distributions of the optical absorption coefficient and the estimation error rate of each layer of the skin 31 for the integral interval are calculated.

In the optical absorption coefficient calculation unit 310, the optical absorption coefficient of each layer in the skin 31 is calculated from the following Equations (9).

$$\begin{cases} N(t_1)\ln\left(\dfrac{N(t_1)}{I(t_1)}\right) = \sum_{i=1}^{n} \mu_i L_i(t_1) \\ \quad\vdots \\ N(t_m)\ln\left(\dfrac{N(t_m)}{I(t_m)}\right) = \sum_{i=1}^{n} \mu_i L_i(t_m) \end{cases} \quad (9)$$

Here, I(t) denotes a light intensity received by the light receiving unit 305 at a time t, N(t) denotes a light intensity at the time t of a model of a time-resolved waveform of short-pulsed light of a specific wavelength $\lambda_k$, $L_i(t)$ denotes an optical path length of an i-th layer at the time t of a model of an optical path length distribution in each layer of the skin, and $\mu_i$ denotes an optical absorption coefficient of the i-th layer.

Here, a first layer is the epidermis, a second layer is the dermis, a third layer is the subcutaneous tissue, $\mu_1$ denotes an optical absorption coefficient of the epidermis, $\mu_2$ denotes an optical absorption coefficient of the dermis, and $\mu_3$ denotes an optical absorption coefficient of the subcutaneous tissue.

The optical absorption coefficient distribution storage unit 311 obtains optical absorption coefficients and estimation error rates in the integral interval defined by the integral interval calculation unit 309 for a combination of the case where non-absorption light intensities N(t) of a plurality of different skin models and optical path length distributions (temporal path-length distributions (TPDs)) of the layers of the skin are used in the optical absorption coefficient calculation unit 310, and stores distributions thereof for the integral interval.

The optical absorption coefficient acquisition unit 312 acquires an optical absorption coefficient based on a glucose concentration corresponding to blood sugar in a main component of the skin at a specific depth by use of a standard for a range of a fluctuation rate of an optical absorption coefficient or the like to a variation of the integral interval from distributions of optical absorption coefficients and estimation error rates for the combination of the case where the non-absorption light intensities N(t) of the plurality of different skin models and the optical path length distributions (TPDs) of the layers of the skin acquired from the optical absorption coefficient distribution storage unit 311 are used.

The concentration calculation unit 313 calculates a concentration of glucose included in a layer of a specific depth from the optical absorption coefficient based on the glucose concentration corresponding to the blood sugar in the main component of the skin of the layer at the specific depth from the surface of the skin acquired by the optical absorption coefficient acquisition unit 312.

The concentration calculation unit 313 calculates a concentration of glucose in a specific layer of the skin from the following Equations (10).

$$\begin{cases} \mu_{a(1)} - \mu_{a(2)} = \sum_{j=1}^{p} g_j(\varepsilon_{j(1)} - \varepsilon_{j(2)}) \\ \quad\vdots \\ \mu_{a(q-1)} - \mu_{a(q)} = \sum_{j=1}^{p} g_j(\varepsilon_{j(q-1)} - \varepsilon_{j(q)}) \end{cases} \quad (10)$$

Here, $\mu_a$ denotes an optical absorption coefficient in an a-th layer, which is a specific layer of the skin, $g_j$ denotes the molar concentration of a j-th component constituting the skin, $\varepsilon_j$ denotes the optical absorption coefficient of the j-th component, p denotes the number of main components constituting the skin, and q denotes the number of types of specific wavelengths $\lambda_k$.

Here, a first layer is the epidermis, a second layer is the dermis, a third layer is the subcutaneous tissue, $\mu_1$ denotes an optical absorption coefficient of the epidermis, $\mu_2$ denotes an optical absorption coefficient of the dermis, and $\mu_3$ denotes an optical absorption coefficient of the subcutaneous tissue.

In the blood sugar measurement apparatus 300, the irradiation unit 304 irradiates the short-pulsed light to the skin, and the light receiving unit 305 receives light backscattered by the skin from the short-pulsed light. The short-pulsed light irradiated by the irradiation unit 304 is uniformly diffused into the skin, and part thereof is backscattered to arrive at the light receiving unit 305. A propagation path of light arriving at the light receiving unit 305 has a banana-shaped three-dimensional shape as indicated by light R of FIG. 2.

In this case, there is a uniform relationship between an input-output distance W between the irradiation unit 304 and the light receiving unit 305 and a penetration depth (a distance between the bottom of a center axis of the banana shape and a body surface (a skin surface)) of the light R penetrating the skin 31. The penetration depth of the light R penetrating the skin 31 is also unambiguously decided by defining the input-output distance W between the irradiation unit 304 and the light receiving unit 305. For example, the penetration depth of the light R becomes 10 mm if the input-output distance W is 10 mm, and the penetration depth of the light R becomes 0.8 mm if the input-output distance W is 0.8 mm.

When the light receiving unit 305 receives the backscattered light, the measurement light intensity acquisition unit 306 acquires an intensity of light received by the light receiving unit 305 at a time t.

Then, the optical path length acquisition unit 307 acquires an optical path length of each layer of the skin at the time t of an optical path length distribution of a skin model from the optical path length distribution storage unit 302, and the non-absorption light intensity acquisition unit 308 acquires an intensity of light at the time t of a time-resolved waveform of short-pulsed light in the skin model from the time-resolved waveform storage unit 303.

Then, the integral interval calculation unit 309 calculates an integral interval, which is a time range (a time width) of an area corresponding to a light intensity of each layer of the skin from a light intensity distribution, based on the light intensity distribution acquired by the measurement light intensity acquisition unit 306, the optical path length distribution acquired by the optical path length acquisition unit 307, and the non-absorption light intensity acquired by the non-absorption light intensity acquisition unit 308.

For example, a start time, an end time, and an increment time of the integral interval are decided using (1) a time from when a light intensity output by the light receiving unit 305 receiving backscattered light is detected at more than minimum detection sensitivity of the measurement light intensity acquisition unit 306 to when a light intensity equal to the minimum detection sensitivity is detected, (2) a time characteristic of a non-absorption light intensity acquired from the time-resolved waveform storage unit 303 storing the non-absorption light intensity obtained by the simulation unit 301, (3) the distance between the light receiving unit 305 and the irradiation unit 304 in contact with a skin surface, and (4) the size and optical characteristics (such as a scattering coefficient, an absorption coefficient, an anisotropy parameter, or a refractive index) of a skin model provided to the simulation unit 301.

Then, the optical absorption coefficient calculation unit 310 calculates an optical absorption coefficient of glucose (a target component) in the dermis (a specific layer) by varying an integral interval, which is a time range (a time width) of an area corresponding to a light intensity of the dermis (a specific layer), for a combination of the skin in the light intensity distribution acquired by the measurement light intensity acquisition unit 306 and a plurality of layers of a model of the time-resolved waveform acquired by the non-absorption light intensity acquisition unit 308.

Then, the optical absorption coefficient distribution storage unit 311 obtains an optical absorption coefficient and an estimation error rate in the integral interval defined by the integral interval calculation unit 309 for a combination of the case where non-absorption light intensities N(t) of a plurality of different skin models and optical path length distributions (TPDs) of the layers of the skin are used in the optical absorption coefficient calculation unit 310, and stores distributions thereof for the integral interval.

Then, the optical absorption coefficient acquisition unit 312 acquires an optical absorption coefficient based on a glucose concentration corresponding to blood sugar in a main component of the skin at a specific depth from the skin surface by use of the distributions of the optical absorption coefficient and the estimation error rate of the specific layer in the integral interval acquired from the optical absorption coefficient distribution storage unit 311 and a standard for a range of a fluctuation rate of the optical absorption coefficient or the like to a variation of the integral interval.

Then, the concentration calculation unit 313 calculates the concentration of glucose included in a layer at a specific depth from the surface of the skin based on the optical absorption coefficient based on the glucose concentration corresponding to the blood sugar in the main component of the skin of the layer at the specific depth from the skin surface acquired by the optical absorption coefficient acquisition unit 312, based on the above-described Equations (10).

According to the above, in the blood sugar measurement apparatus 300, the integral interval calculation unit 309 calculates an integral interval, which is a time range (a time width) of an area corresponding to a light intensity of each layer of the skin from the above-described light intensity distribution, based on the light intensity distribution acquired by the measurement light intensity acquisition unit 306, the optical path length distribution acquired by the optical path length acquisition unit 307, and the non-absorption light intensity acquired by the non-absorption light intensity acquisition unit 308, and the optical absorption coefficient calculation unit 310 calculates an optical absorption coefficient of glucose (a target component) in the dermis (a specific layer) by varying an integral interval, which is a time range (a time width) of an area corresponding to a light intensity of the dermis (a specific layer), for a combination of the light intensity distribution acquired by the measurement light intensity acquisition unit 306 and the plurality of layers of the skin of a model of the time-resolved waveform acquired by the non-absorption light intensity acquisition unit 308, so that it is possible to select an optical absorption coefficient of the dermis (a specific layer) in a combination close to an optical path length distribution of a skin structure. Therefore, it is possible to accurately measure an optical absorption amount of the glucose, that is, a glucose concentration, in the dermis, and consequently it is possible to non-invasively and accurately determine the glucose concentration in the dermis.

Next, an operation of the blood sugar measurement apparatus 300 will be described.

Before a blood sugar level is measured, the blood sugar measurement apparatus 300 needs to pre-calculate an optical path length distribution and a time-resolved waveform in each layer of the skin model.

Here, a method of calculating the optical path length distribution and the time-resolved waveform of the skin model will be described.

Initially, the simulation unit 301 generates the skin model. The skin model is generated by deciding a light scattering coefficient, an optical absorption coefficient, and a thickness of each layer of the skin. Here, if a portion of the skin is specified, it is preferable that a scattering coefficient and a thickness of each layer in the specified skin portion be decided by pre-taking samples because an individual difference is small. The thickness of the epidermis 32 is about 0.3 mm, the thickness of the dermis 33 is about 1.2 mm, and the thickness of the subcutaneous tissue 34 is about 3.0 mm.

The optical absorption coefficient of the skin model used here is assumed to be zero. This is because an optical absorption amount is calculated using the skin model.

When the skin model is generated, the simulation unit 301 performs a simulation by irradiating light to the skin model. At this time, it is necessary to decide a distance W between a position of the irradiation unit 304 and a position of the light receiving unit 305. The simulation is performed, for example, using a Monte-Carlo method.

The simulation based on the Monte-Carlo method is performed, for example, as follows.

First, the simulation unit 301 performs a calculation operation by irradiating photons to the skin model by designating a model of irradiated light as photons (a light flux). The photons irradiated to the skin model move within the skin model. At this time, a distance L and a direction θ until the photons move to the next point are decided by a random number R. The simulation unit 301 calculates the distance L until the photons move to the next point by Equation (11).

$$L = ln(R/\mu_s) \quad (11)$$

Here, ln(A) denotes a natural logarithm of A, and $\mu_s$ denotes a scattering coefficient of an s-th layer (one of the epidermis, the dermis, and the subcutaneous tissue) of the skin model.

The simulation unit 301 calculates the direction θ until the photons move to the next point by Equation (12).

$$\theta = \cos^{-1}\left[\frac{1}{2g}\left\{1 + g^2 - \left(\frac{1-g^2}{1+g-2gR}\right)^2\right\}\right] \quad (12)$$

Here, g is an anisotropy parameter, which is an average of a cosine (cos) of a scattering angle. The anisotropy parameter of the skin is about 0.9.

The simulation unit 301 iterates the calculations using the above-described Equations (11) and (12) every unit time, thereby calculating a moving path of the photons from the irradiation unit 304 to the light receiving unit 305. The simulation unit 301 calculates a moving distance for a plurality of photons. For example, the simulation unit 301 calculates a moving distance for 108 photons.

The simulation unit 301 classifies a moving path of each photon arriving at the light receiving unit 305 according to each layer through which the moving path passes. Also, the simulation unit 301 calculates an average length of the moving path of photons arriving every unit time for each classified layer, thereby varying a scattering coefficient of each layer of the skin to create an optical path length distribution (TPD)

corresponding to a varied scattered coefficient of each layer of the skin. The optical path length distribution (TPD) created as described above is stored in the optical path length distribution storage unit 302.

Also, the simulation unit 301 calculates a time-resolved waveform of the skin model by calculating the number of photons arriving at the light receiving unit 305 every unit of time.

Figure 10:
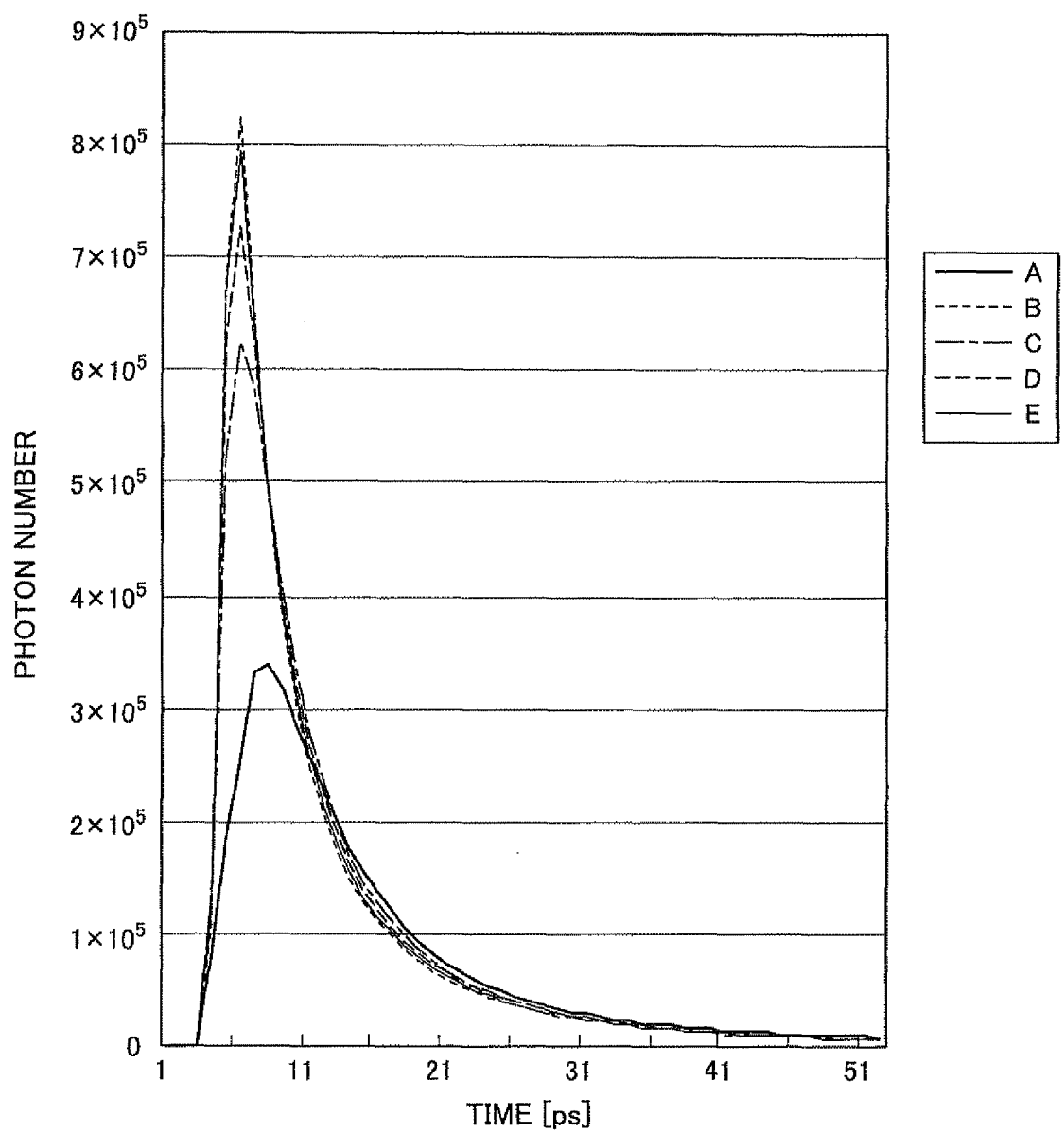
FIG. 10 is a diagram showing a time-resolved waveform of a non-absorption light intensity obtained by a simulation unit in accordance with the fourth embodiment of the present invention.

FIG. 10 is a diagram showing a time-resolved waveform of a non-absorption light intensity (which is equal to the number of received photons) N(t) obtained by the simulation unit 301. In FIG. 10, a skin model of three layers of the epidermis, the dermis, and the subcutaneous tissue is used, and the absorption coefficient of the dermis is varied until the absorption coefficient of the epidermis is varied from 25% to 150%. In FIG. 10, A indicates 25%, B indicates 50%, C indicates 75%, D indicates 100%, E indicates 125%, and F indicates 150%.

Here, the absorption coefficient of the epidermis is varied from 25% to 150%, and the optical path length distribution (TPD) corresponding to each varied scattered coefficient is created. Therefore, the optical path length distribution (TPD) is created in correspondence with the absorption coefficient varying from 25% to 150%.

According to FIG. 10, it can be seen that an amplitude is equal to or less than 5% for a maximum value (peak value) of the number of photons or the light intensity at about 30 ps, and is close to a true value.

Figure 11:
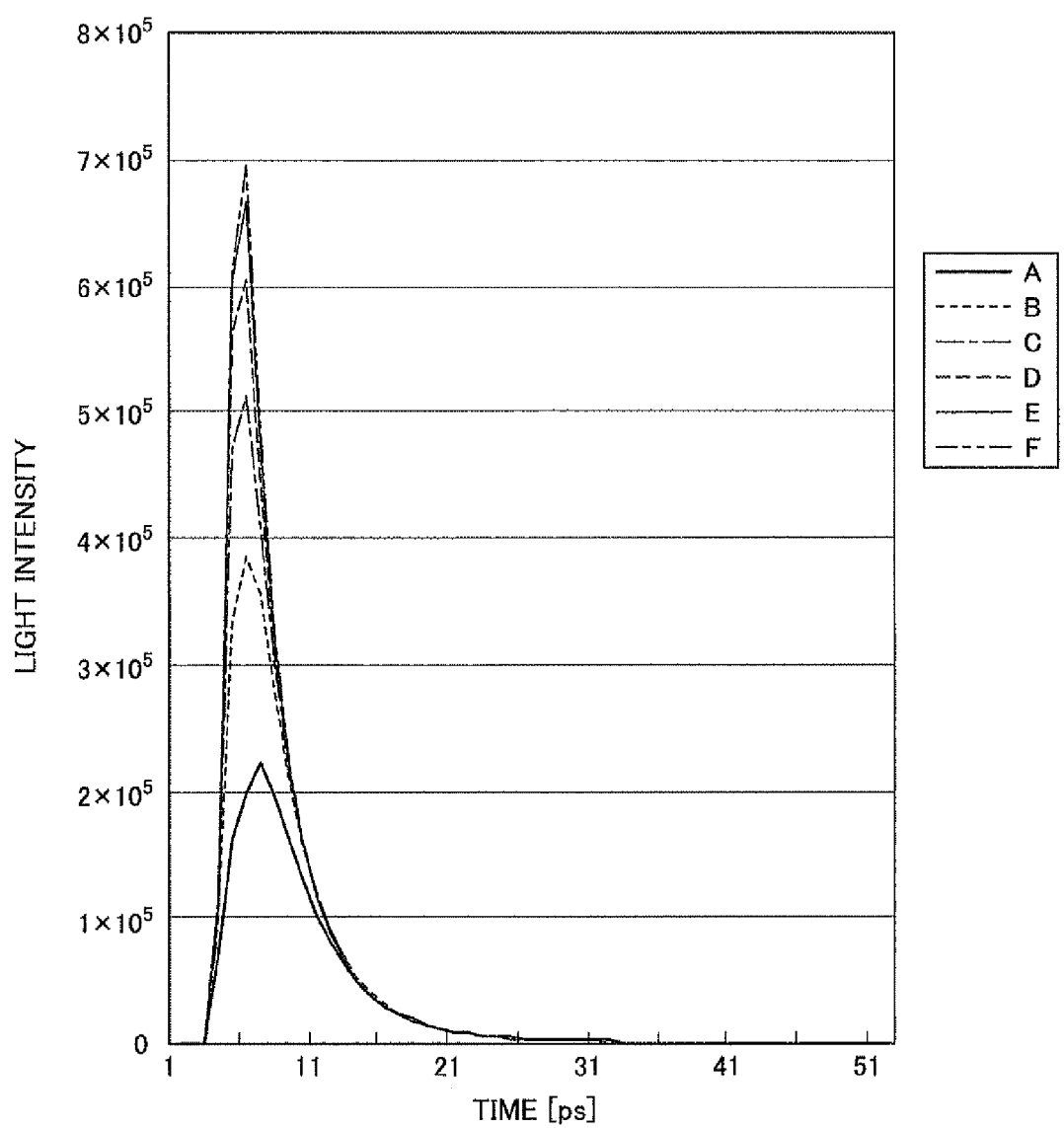
FIG. 11 is a diagram showing a time-resolved waveform of an absorption light intensity obtained by a simulation along with a non-absorption light intensity and an optical path length distribution (TPD) of FIG. 10 in a linear scale.
Figure 12:
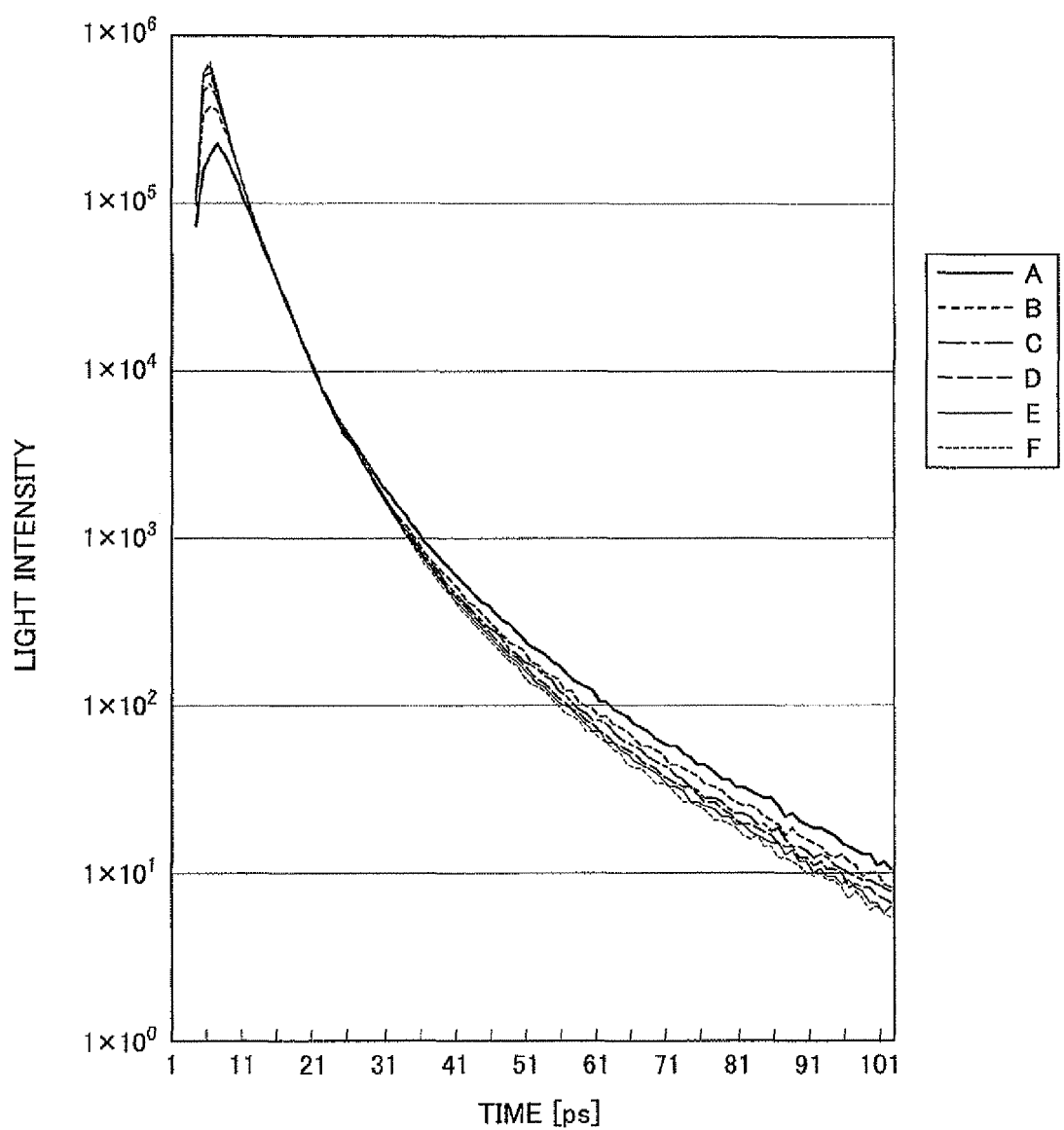
FIG. 12 is a diagram showing the time-resolved waveform of FIG. 11 in a log scale.

FIG. 11 is a diagram showing a time-resolved waveform of an absorption light intensity I(t) obtained by a simulation along with a non-absorption light intensity N(t) and an optical path length distribution (TPD) of FIG. 10 in a linear scale. FIG. 12 is a diagram showing the time-resolved waveform of FIG. 11 in a log scale.

According to FIGS. 11 and 12, it can be seen that the absorption coefficient of the dermis is largely varied by varying the absorption coefficient of the epidermis. Therefore, it can be seen that the reduction of about three digits to the peak value is made when the absorption coefficient of the epidermis to the absorption coefficient of the dermis is 25% at about 50 ps.

According to the process as described above, the simulation unit 301 calculates optical path length distributions and time-resolved waveforms of a plurality of different skin models. At this time, it is preferable that the simulation unit 301 calculate an optical path length distribution and a time-resolved waveform for a wavelength at which a difference between absorption spectra of the main components (such as water, protein, lipid, and glucose) is large.

When the simulation unit 301 calculates optical path length distributions and time-resolved waveforms of the plurality of different skin models, the optical path length distribution storage unit 302 stores information on the calculated optical path length distributions and the time-resolved waveform storage unit 303 stores information on the time-resolved waveforms.

Figure 13:
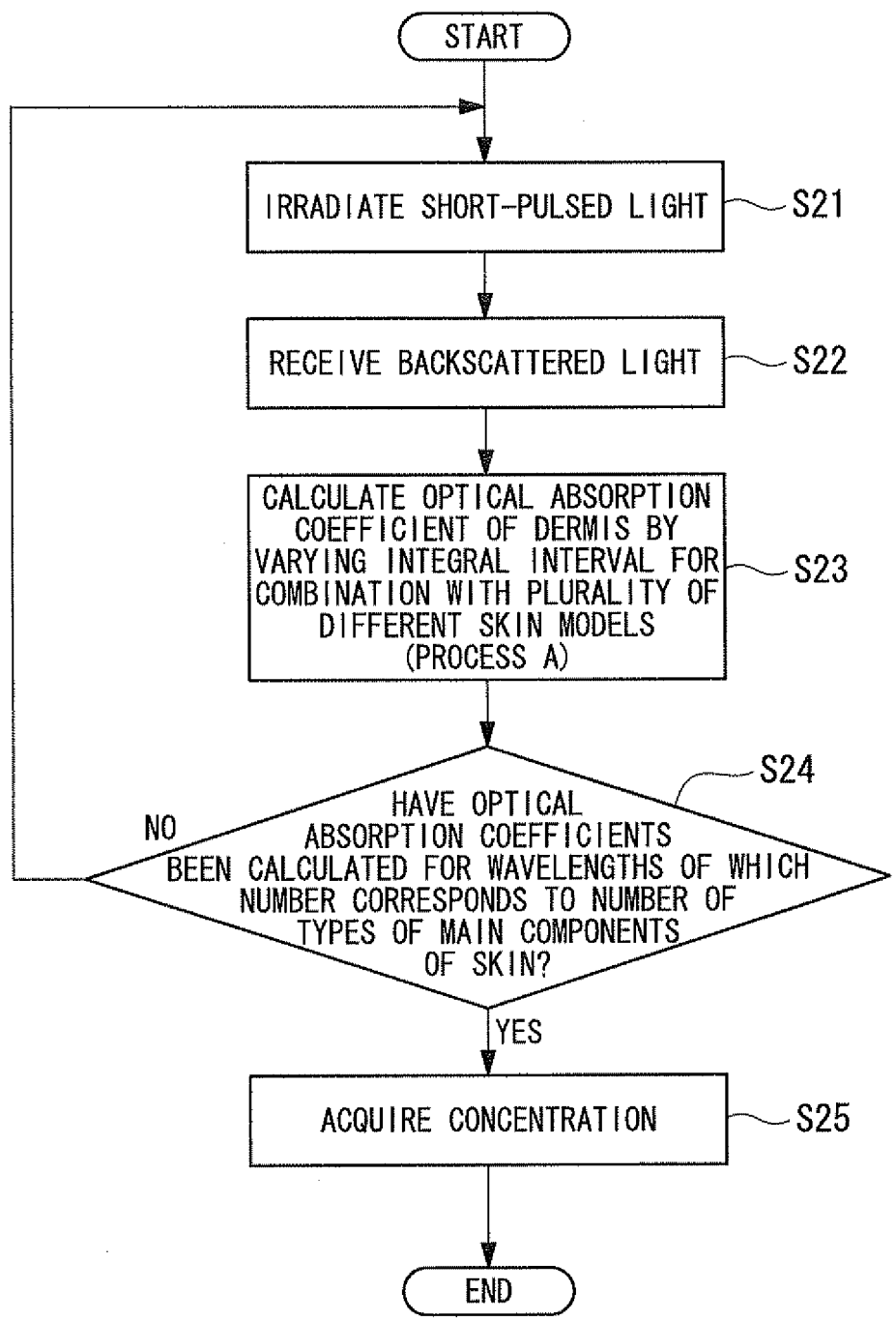
FIG. 13 is a flowchart showing a process of measuring a blood sugar value by the blood sugar value measurement apparatus in accordance with the fourth embodiment of the present invention.

Next, an operation in which the blood sugar measurement apparatus 300 measures a blood sugar level will be described based on FIGS. 13 and 14.

First, when a person to be measured applies the blood sugar measurement apparatus 300 to skin such as on a wrist as shown in FIG. 2 and operates the blood sugar measurement apparatus 300 by pressing a measurement start switch (not shown) or the like, the irradiation unit 304 irradiates short-pulsed light of a wavelength $\lambda_k$ to the skin 31 (step S21).

Here, it is preferable that the wavelength $\lambda_k$ be one of a plurality of wavelengths for which the simulation unit 301 calculates optical path length distributions and time-resolved waveforms.

For example, it is preferable that an optical path length distribution and a time-resolved waveform be calculated for light of a wavelength at which an optical absorption coefficient of a specific component in a certain main component among the main components constituting the skin 31 becomes greater than optical absorption coefficients of other components, that is, for light of a wavelength at which a minimum value of the optical absorption coefficient of the specific component is largely different from those of the other components.

When the irradiation unit 304 irradiates short-pulsed light of the wavelength $\lambda_k$, the light receiving unit 305 receives light backscattered by the skin 31 after irradiation from the irradiation unit 304 (step S22).

At this time, the light receiving unit 305 stores a received light intensity in an internal memory (not shown) every unit time (for example, at times $t_1$ to $t_m$ of every 1 picosecond) from the initiation of irradiation.

Then, an optical absorption coefficient of the dermis 33 is calculated by varying an integral interval for a combination with a plurality of different skin models (process A: step S23).

Figure 14:
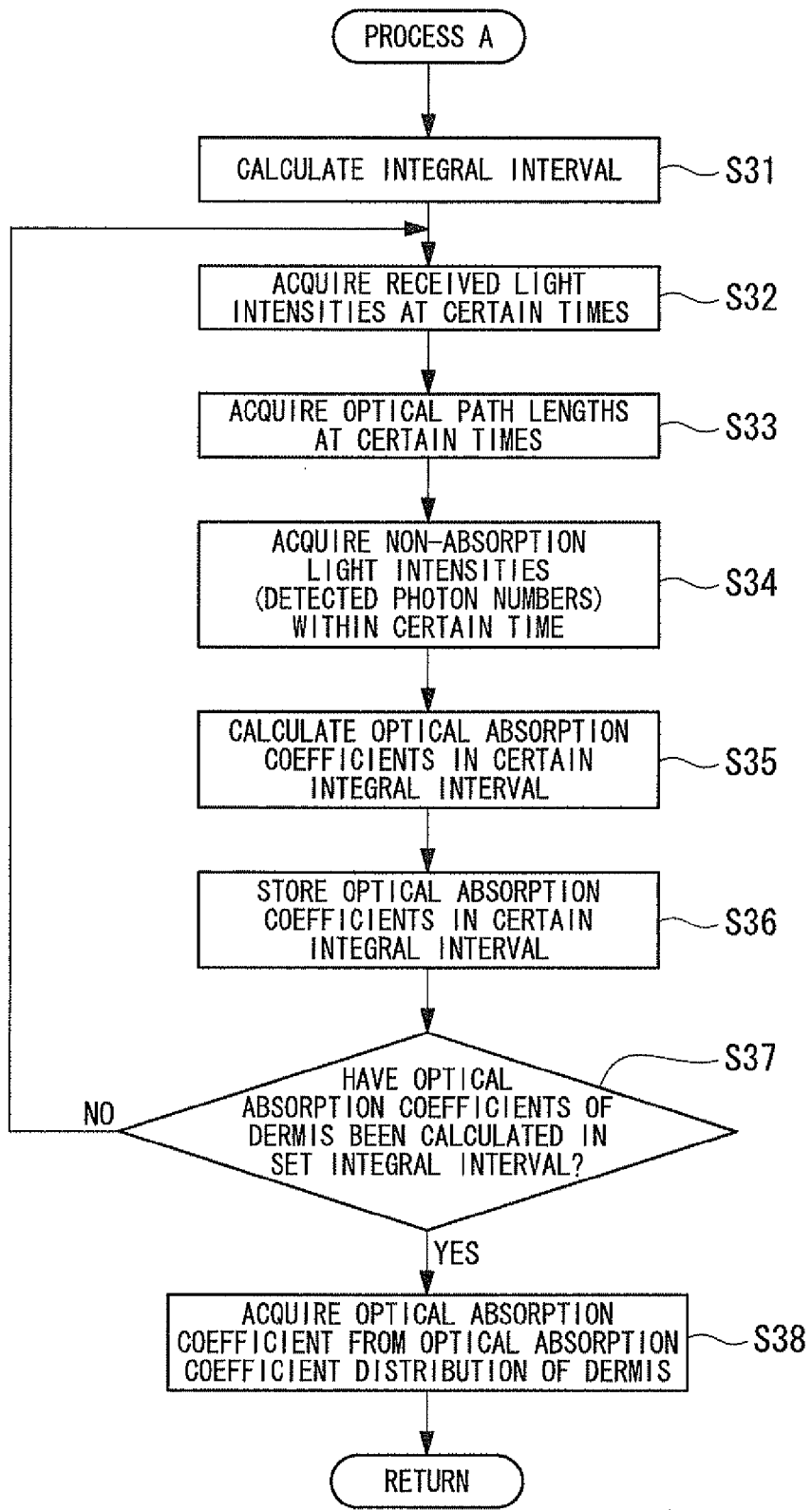
FIG. 14 is a flowchart showing a process of measuring a blood sugar value by the blood sugar value measurement apparatus in accordance with the fourth embodiment of the present invention.

Step S23 is performed by an operation shown in FIG. 14.

The integral interval calculation unit 309 calculates an integral interval, which is a time range (a time width) of an area corresponding to a light intensity of each layer of the skin from the light intensity distribution, based on the light intensity distribution acquired by the measurement light intensity acquisition unit 306, the optical path length distribution acquired by the optical path length acquisition unit 307, and the non-absorption light intensity acquired by the non-absorption light intensity acquisition unit 308.

Here, the integral interval calculation unit 309 calculates an integral interval by use of (1) a time from when a light intensity output by the light receiving unit 305 receiving backscattered light is detected at more than minimum detection sensitivity of the measurement light intensity acquisition unit 306 to when a light intensity equal to the minimum detection sensitivity is detected, (2) a time characteristic of a non-absorption light intensity acquired from the time-resolved waveform storage unit 303 storing the non-absorption light intensity obtained by the simulation unit 301, (3) the distance between the light receiving unit 305 and the irradiation unit 304 in contact with a skin surface, and (4) the size and optical characteristics (such as a scattering coefficient, an absorption coefficient, an anisotropy parameter, or a refractive index) of a skin model provided to the simulation unit 301.

More specifically, a start time, an end time, and an increment time of the integral interval are calculated (step S31).

When the light receiving unit 305 completes light reception, the measurement light intensity acquisition unit 306 acquires received light intensities, of which the number is the same as the number of different skin models, at certain times t from received light intensities recorded in the internal memory (step S32).

For example, when the concentration measurement is performed using four types of wavelengths in the three layers of the skin as a plurality of different skin models, the received light intensities $I(t_1)$ to $I(t_3)$ are acquired at three different times $t_1$ to $t_3$. Here, the received light intensities of which the number is the same as the number of layers of the skin are acquired because the absorption coefficient of each layer of the skin is calculated by simultaneous equations in a process to be described later.

It is preferable that the times $t_1$ to $t_3$ at which the measurement light intensity acquisition unit 306 acquires the light intensities be those at which optical light path length distributions of the layers of the skin peak. That is, it is preferable that each light intensity be acquired at a time obtained by adding a time at which the optical path length of each layer of the skin is maximized in FIG. 3 to a time at which the irradiation unit 304 irradiates short-pulsed light.

When the measurement light intensity acquisition unit 306 acquires the received light intensities $I(t_1)$ to $I(t_3)$, the optical path length acquisition unit 307 acquires optical path lengths $L_1(t_1)$ to $L_1(t_3)$, $L_2(t_1)$ to $L_2(t_3)$, and $L_3(t_1)$ to $L_3(t_3)$ of the layers of the skin at the times $t_1$ to $t_3$ from an optical path length distribution of a wavelength $\lambda_1$ stored in the optical path length distribution storage unit 302 (step S33).

When the measurement light intensity acquisition unit 306 acquires the received light intensities $I(t_1)$ to $I(t_3)$, the non-absorption light intensity acquisition unit 308 acquires light intensities at predetermined times of the plurality of different skin models of a time-resolved waveform of short-pulsed light, for example, detected photon numbers (non-absorption light intensities) $N(t_1)$ to $N(t_3)$ at the times $t_1$ to $t_3$, from a time-resolved waveform of the wavelength $\lambda_1$ stored by the time-resolved waveform storage unit 303 (step S34).

When the optical path length acquisition unit 307 acquires the optical path lengths of the layers of the skin and the non-absorption light intensity acquisition unit 308 acquires the detected photon numbers (non-absorption light intensities) $N(t_1)$ to $N(t_3)$, the optical absorption coefficient calculation unit 310 calculates an optical absorption coefficient of glucose in the dermis by varying an integral interval, which is a time range (a time width) of an area corresponding to a light intensity of the dermis, for a combination of a light intensity distribution acquired by the measurement light intensity acquisition unit 306 and a plurality of layers of the skin of a model of a time-resolved waveform acquired by the non-absorption light intensity acquisition unit 308.

Here, optical absorption coefficients $\mu_1$ to $\mu_3$ of the layers of the skin based on Equations (13) are calculated in the integer interval calculated by the integral interval calculation unit 309 (step S35). Here, the optical absorption coefficient $\mu_1$ indicates the optical absorption coefficient of the epidermis. The optical absorption coefficient $\mu_2$ indicates the optical absorption coefficient of the dermis. The optical absorption coefficient $\mu_3$ indicates the optical absorption coefficient of the subcutaneous tissue.

$$\begin{cases} N'(t_1)\ln\left(\dfrac{N'(t_1)}{I'(t_1)}\right) = \sum_{i=1}^{3} \mu_i L_i(t_1) \\ N'(t_2)\ln\left(\dfrac{N'(t_2)}{I'(t_2)}\right) = \sum_{i=1}^{3} \mu_i L_i(t_2) \\ N'(t_3)\ln\left(\dfrac{N'(t_3)}{I'(t_3)}\right) = \sum_{i=1}^{3} \mu_i L_i(t_3) \end{cases} \quad (13)$$

$$\text{where } N'(t) = \frac{N(t)}{N_{in}} \text{ and } I'(t) = \frac{I(t)}{I_{in}}$$

Here, $\ln(A)$ denotes a natural logarithm of A, and $N(t)$ denotes the light intensity at a time t of a model of a time-resolved waveform of short-pulsed light of a specific wavelength $\lambda_k$. $I_{in}$ denotes a light intensity of the short-pulsed light irradiated by the irradiation unit 304. $N_{in}$ denotes the number of photons according to irradiation in a simulation performed by the simulation unit 301.

When the optical absorption coefficient calculation unit 310 calculates the optical absorption coefficients $\mu_1$ to $\mu_3$ of the layers of the skin in a certain integral interval, the optical absorption coefficient distribution storage unit 311 stores the optical absorption coefficients $\mu_1$ to $\mu_3$ of the layers of the skin in the certain integral interval calculated by the optical absorption coefficient calculation unit 310.

Figure 15:
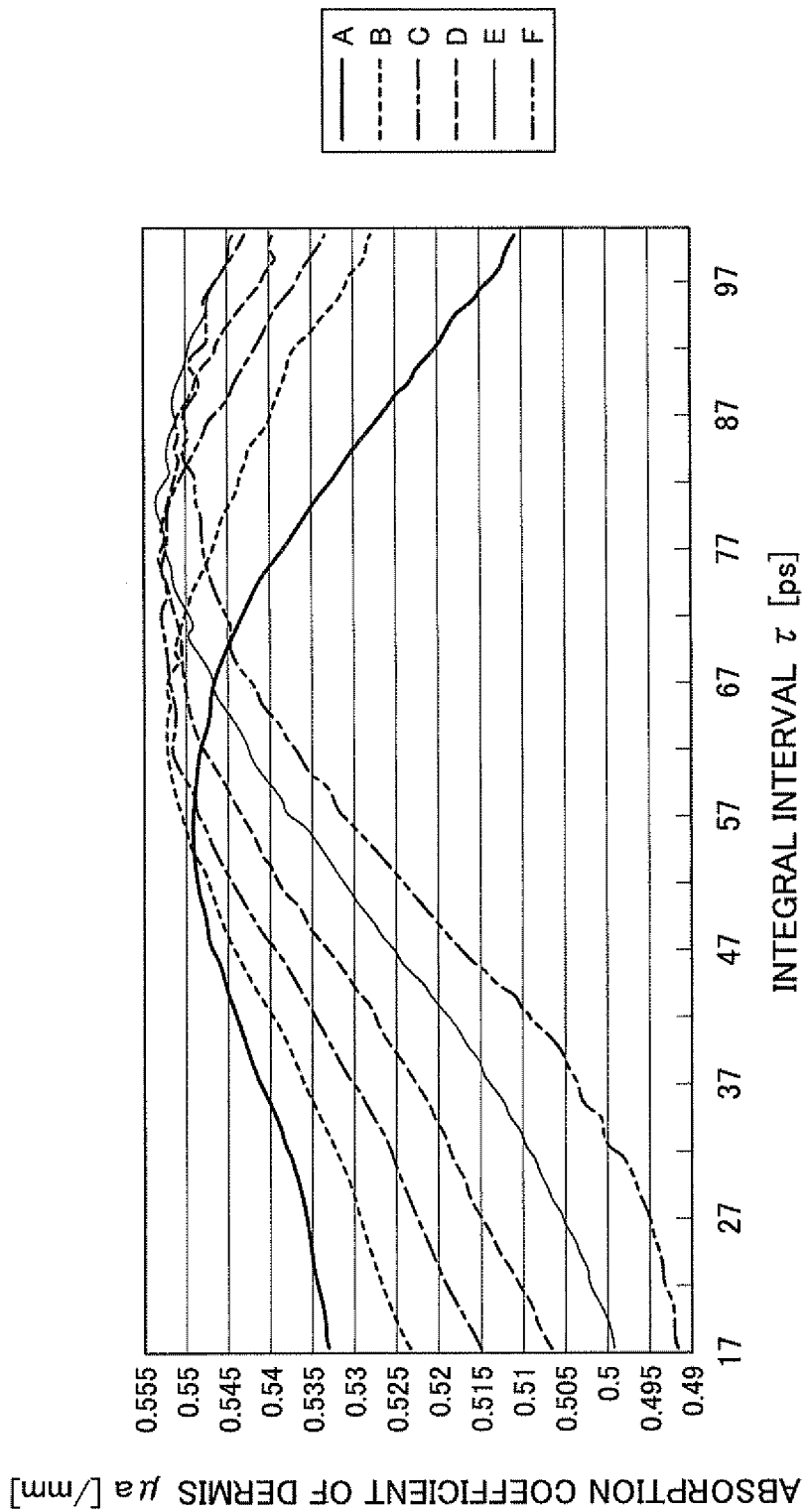
FIG. 15 is a diagram showing a relationship between an optical absorption coefficient of the dermis and an integral interval.

FIG. 15 is a diagram showing a relationship between an optical absorption coefficient of the dermis and an integral interval. FIG. 15 shows a relationship between an integral interval and an optical absorption coefficient of the dermis when a skin model of three layers of the epidermis, the dermis, and the subcutaneous tissue is used and a scattering coefficient of the epidermis to the optical absorption coefficient of the dermis is varied by −50% to +200%© to literature data. In FIG. 15, A indicates −50%, B indicates −0%, C indicates +50%, D indicates +100%, E indicates +150%, and F indicates +200%.

Here, a non-absorption light intensity $N(t)$ and an optical path length distribution (TPD) of each layer of the skin model are varied by varying the scattering coefficient of the epidermis.

According to FIG. 15, it can be seen that characteristics of the optical absorption coefficient of the dermis are obtained when different non-absorption light intensities $N(t)$ and optical path length distributions (TPDs) of the layers of the skin model are used by varying the integral interval.

The scattering coefficient of the dermis in the skin structure serving as an object upon measurement is unknown. However, in this embodiment, because an optical absorption coefficient of glucose in the dermis is calculated by varying an integral interval, which is a time range (a time width) of an area corresponding to the light intensity of the dermis, for a combination of a light intensity distribution acquired by the measurement light intensity acquisition unit 306 and a plurality of layers of the skin of a model of a time-resolved waveform acquired by the non-absorption light intensity acquisition unit 308, it is possible to select an optical absorption coefficient of the dermis in a combination close to an optical path length distribution (TPD) of the skin structure.

When the optical absorption coefficient calculating unit 310 calculates the optical absorption coefficients $\mu_1$ to $\mu_3$ of the layers of the skin in a certain integral interval, the optical absorption coefficient calculation unit 310 determines whether or not the optical absorption coefficients of the dermis in the set integral interval have been calculated (step S37).

In this embodiment, because a blood sugar level is measured by designating the main components of the skin as four types of water, protein, lipid, and glucose, the optical absorption coefficient calculation unit 310 determines whether or not the optical absorption coefficients $\mu_1$ to $\mu_3$ for four types of wavelengths $\lambda_1$ to $\lambda_4$ have been calculated. Here, the wavelengths $\lambda_1$ to $\lambda_4$ are selected from among a plurality of wavelengths for which the simulation unit 301 has calculated optical path length distributions and time-resolved waveforms.

If the optical absorption coefficient calculation unit 310 determines that there is an uncalculated optical absorption coefficient among the optical absorption coefficients $\mu_1$ to $\mu_3$ of the dermis in the set integral interval (step S37: NO), the process returns to step S32 of acquiring received light intensities at certain times, the uncalculated optical absorption coefficient of the dermis is calculated, and the determination (step S37) as to whether or not the optical absorption coefficients of the dermis in the set integral interval have been calculated is re-performed.

On the other hand, if the optical absorption coefficient calculation unit 310 determines that the optical absorption coefficients $\mu_1$ to $\mu_3$ of the dermis in the set integral interval have been calculated (step S37: YES), an optical absorption coefficient is acquired from the optical absorption coefficient distribution of the dermis (step S38), The optical absorption coefficient acquisition unit 312 determines whether or not optical absorption coefficients of which the number is the number of wavelengths corresponding to the number of types of main components of the skin have been calculated (step S24).

Here, if the optical absorption coefficient acquisition unit 312 determines that optical absorption coefficients of which the number is the number of wavelengths corresponding to the number of types of main components of the skin have not been calculated (step S24: NO), the process returns to step S21 of irradiating short-pulsed light, an uncalculated optical absorption coefficient of which the number is the number of wavelengths corresponding to the number of types of the main components of the skin is calculated, and the determination (step S24) as to whether or not the optical absorption coefficients have been calculated is re-performed.

On the other hand, if the optical absorption coefficient acquisition unit 312 determines that optical absorption coefficients of which the number is the number of wavelengths corresponding to the number of types of main components of the skin have been calculated (step S24: YES), the concentration calculation unit 313 calculates the concentration of glucose included in the dermis (step S25).

The concentration calculation unit 313 calculates the concentration of glucose included in the dermis based on the following Equations (14).

$$\begin{cases} \mu_{2(1)} - \mu_{2(2)} = \sum_{i=1}^{4} g_i(\varepsilon_{i(1)} - \varepsilon_{i(2)}) \\ \vdots \\ \mu_{2(4)} - \mu_{2(1)} = \sum_{i=1}^{4} g_i(\varepsilon_{i(4)} - \varepsilon_{i(1)}) \end{cases} \quad (14)$$

Here, $\mu_{2(1)}$ to $\mu_{2(4)}$ denote optical absorption coefficients of the wavelengths $\lambda_1$ to $\lambda_4$ in the dermis. $g_1$ to $g_4$ denote molar concentrations of water, protein, lipid and glucose that are the main components of the skin in the dermis. $\varepsilon_{1(1)}$ to $\varepsilon_{1(4)}$ denote molar extinction coefficients of water for the wavelengths $\lambda_1$ to $\lambda_4$. $\varepsilon_{2(1)}$ to $\varepsilon_{2(4)}$ denote molar extinction coefficients of protein for the wavelengths $\lambda_1$ to $\lambda_4$. $\varepsilon_{3(1)}$ to $\varepsilon_{3(4)}$ denote molar extinction coefficients of lipid for the wavelengths to $\lambda_1$ to $\lambda_4$. $\varepsilon_{4(1)}$ to $\varepsilon_{4(4)}$ denote molar extinction coefficients of glucose for the wavelengths $\lambda_1$ to $\lambda_4$.

That is, the molar concentration of glucose included in the dermis can be acquired by calculating $g_4$ of Equations (14).

The molar concentration of glucose can be obtained by Equations (14) for the same reason as in the first embodiment.

The blood sugar measurement apparatus 300 may internally include a computer system (not shown). Processing operations of the steps described above are stored in a computer-readable recording medium in the form of a program. The above-described processing operations can be performed by the computer reading and executing the program.

Here, the computer-readable recording medium may be a magnetic disk, a magneto-optical disc, a CD-ROM, a DVD-ROM, a semiconductor memory, or the like.

The computer program may be distributed to the computer through a communication line, and the computer receiving the distribution may execute the program.

The above-described program may be used to implement a part of the above-described function.

In addition, the program may be a differential file (differential program) capable of implementing the above-described function in combination with a program already recorded in the computer system.

According to this embodiment as described above, because the integral interval calculation unit 309 calculates an integral interval, which is a time range (a time width) of an area corresponding to a light intensity of each layer of the skin from the light intensity distribution, based on the light intensity distribution acquired by the measurement light intensity acquisition unit 306, the optical path length distribution acquired by the optical path length acquisition unit 307, and the non-absorption light intensity acquired by the non-absorption light intensity acquisition unit 308, and the optical absorption coefficient calculation unit 310 calculates an optical absorption coefficient of glucose in the dermis by varying the integral interval, it is possible to select an optical absorption coefficient of the dermis in a combination close to an optical path length distribution of a skin structure. Therefore, it is possible to accurately measure an optical absorption amount of the glucose, that is, a glucose concentration, in the dermis of the skin, and consequently it is possible to non-invasively and accurately determine the glucose concentration in the dermis.

Also, it is possible to improve an accuracy of measurement of a concentration of glucose in the dermis by varying the integral interval.

Although the simulation unit 301 performs a simulation by irradiating light to a skin model having an optical absorption coefficient of 0 in this embodiment, the same function and effect as in this embodiment can be provided even when the simulation unit 301 is not provided if results of a simulation performed by the simulation unit 301, which irradiates light to the skin model having the optical absorption coefficient of 0, are stored in the optical path length distribution storage unit 302 and the time-resolved waveform storage unit 303.

Fifth Embodiment

Figure 16:
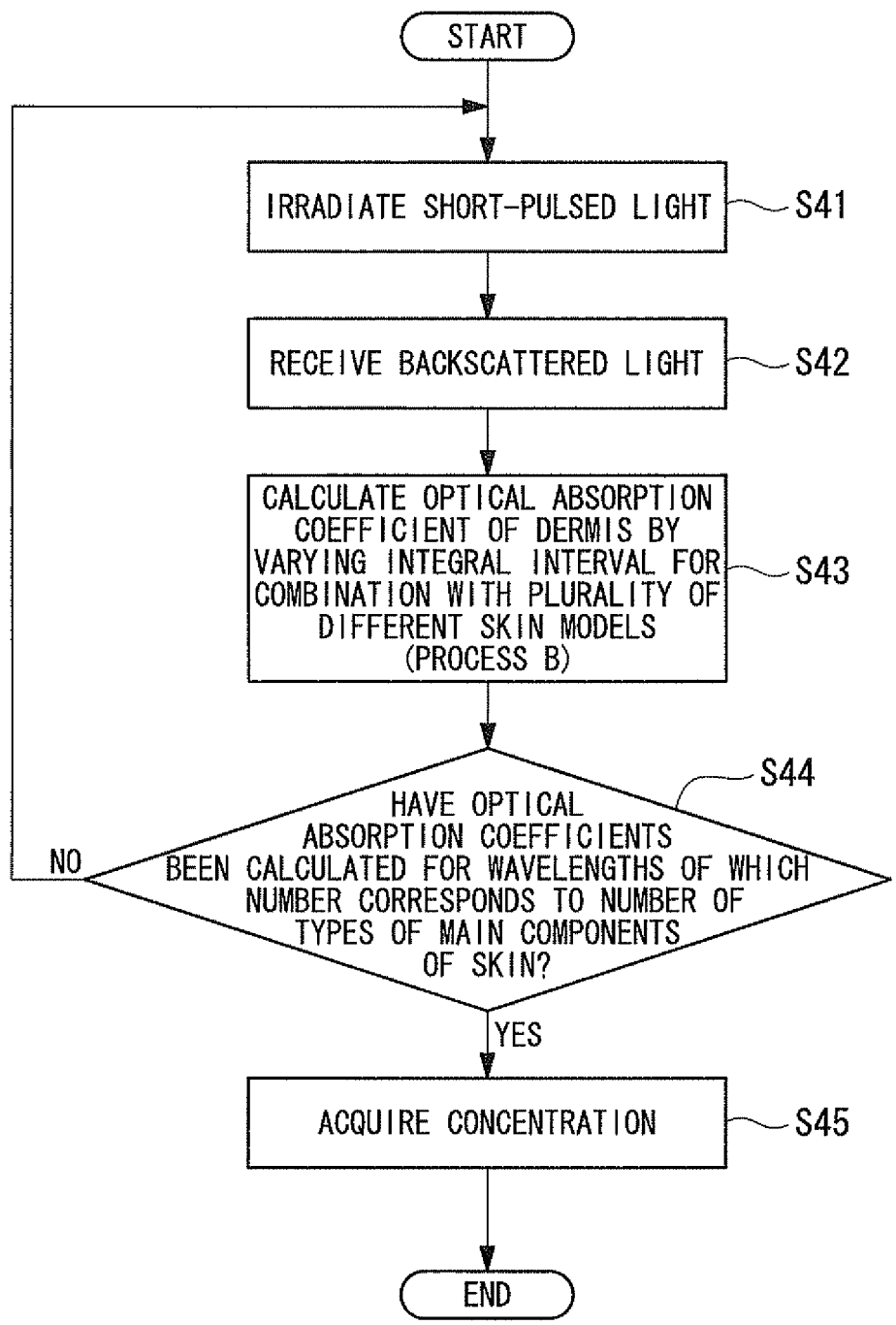
FIGS. 16 and 17 are flowcharts showing an operation in which a blood sugar measurement apparatus (a concentration determination apparatus) of the fifth embodiment of the present invention measures a blood sugar level.
Figure 17:
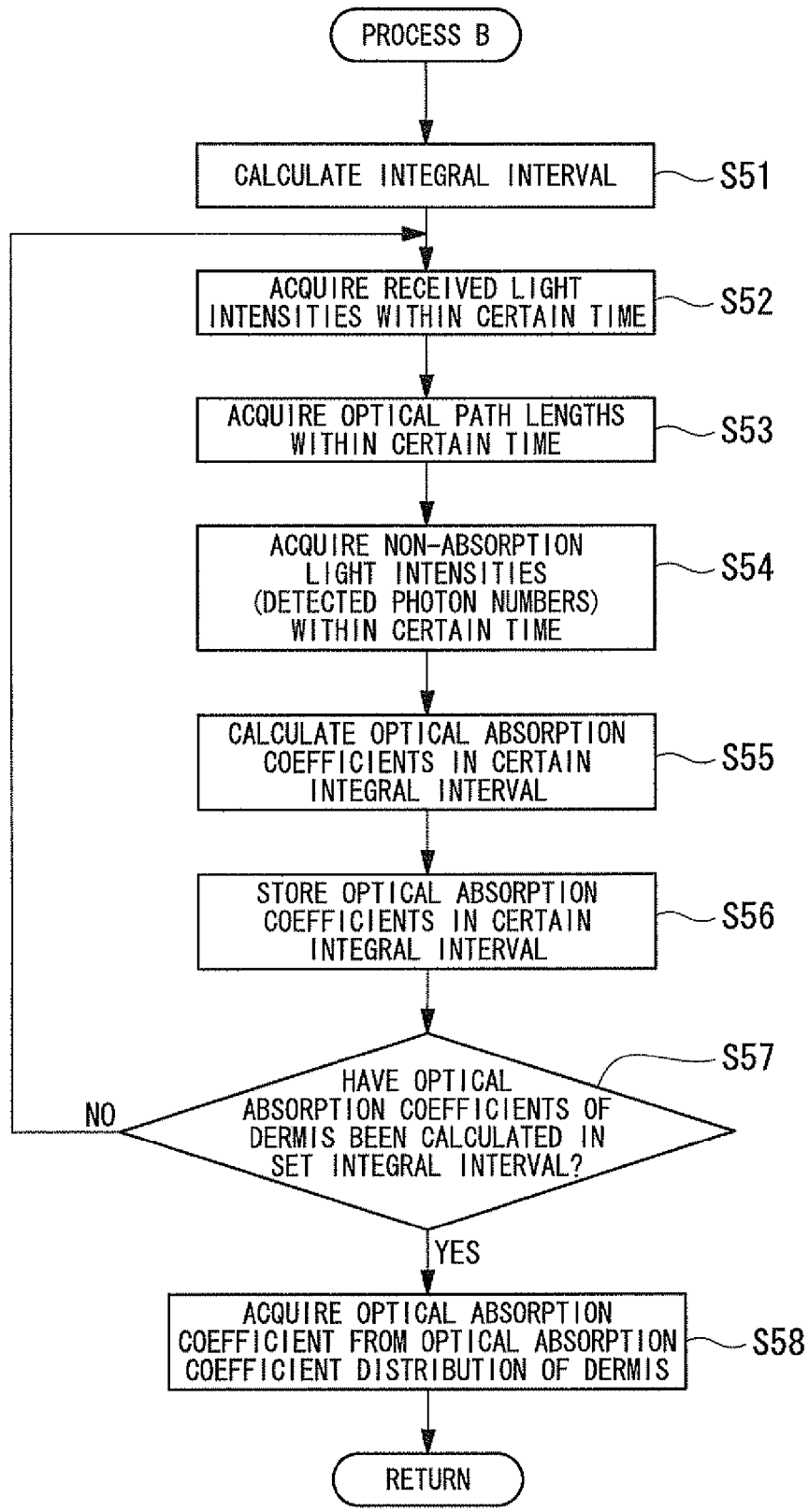

FIGS. 16 and 17 are flowcharts showing an operation in which a blood sugar measurement apparatus (a concentration determination apparatus) of the fifth embodiment of the present invention measures a blood sugar level.

The blood sugar measurement apparatus of this embodiment has the same configuration as the blood sugar measurement apparatus 300 of the fourth embodiment, but operations of the optical path length acquisition unit 307, the non-absorption light intensity acquisition unit 308, the measurement light intensity acquisition unit 306, and the optical absorption coefficient calculation unit 310 are different from those of the blood sugar measurement apparatus 300 of the fourth embodiment.

Next, an operation in which the blood sugar measurement apparatus of this embodiment measures a blood sugar level will be described.

First, when a person to be measured operates the blood sugar measurement apparatus 300, the irradiation unit 304 irradiates short-pulsed light of a wavelength $\lambda_k$ to skin 31 (step S41).

For example, it is preferable that the wavelength $\lambda_k$ be one of a plurality of wavelengths for which the simulation unit 301 calculates optical path length distributions and time-resolved waveforms.

When the irradiation unit 304 irradiates short-pulsed light of the wavelength $\lambda_k$, the light receiving unit 305 receives light backscattered by the skin after irradiation from the irradiation unit 304 (step S42).

At this time, the light receiving unit 305 stores a received light intensity in an internal memory (not shown) every unit time (for example, every 1 picosecond) from the initiation of irradiation.

Then, an optical absorption coefficient of the dermis is calculated by varying an integral interval for a combination with a plurality of different skin models (process B: step S43).

Step S43 is performed by an operation shown in FIG. 17.

The integral interval calculation unit 309 calculates an integral interval, which is a time range of an area corresponding to a light intensity of each layer of the skin from a light intensity distribution, based on the light intensity distribution acquired by the measurement light intensity acquisition unit 306, the optical path length distribution acquired by the optical path length acquisition unit 307, and the non-absorption light intensity acquired by the non-absorption light intensity acquisition unit 308 (step S51).

When the light receiving unit 305 completes light reception, the measurement light intensity acquisition unit 306 acquires time distributions of received light intensities, of which the number is the same as the number of different skin models, for a time from a certain time from received light intensities recorded in the internal memory of the light receiving unit 305 (step S52).

When the measurement light intensity acquisition unit 306 acquires the time distributions of the received light intensities for the time $\tau$, the optical path length acquisition unit 307 acquires optical path lengths $L_1$ to $L_3$ of the layers of the skin for the time $\tau$ from an optical path length distribution of wavelengths $\lambda_k$ stored by an optical path length distribution storage unit 302 (step S53).

When the measurement light intensity acquisition unit 306 acquires the received light intensities for the time $\tau$, the non-absorption light intensity acquisition unit 308 acquires detected photon numbers (non-absorption light intensities) for the time $\tau$ from the certain time from time-resolved waveforms of wavelengths $\lambda_k$ stored by the time-resolved waveform storage unit 303 (step S54).

When the optical path length acquisition unit 307 acquires the optical path lengths of the layers of the skin and the non-absorption light intensity acquisition unit 308 acquires the detected photon numbers, the optical absorption coefficient calculation unit 310 calculates an optical absorption coefficient of glucose in the dermis by varying an integral interval, which is a time range (a time width) of an area corresponding to a light intensity of the dermis, for a combination of a light intensity distribution acquired by the measurement light intensity acquisition unit 306 and a plurality of layers of the skin of a model of a time-resolved waveform acquired by the non-absorption light intensity acquisition unit 308.

Here, optical absorption coefficients $\mu_1$ to $\mu_3$ of the layers of the skin in the integral interval calculated by the integral interval calculation unit 309 are calculated based on Equations (15) (step S55). Here, the optical absorption coefficient $\mu_1$ indicates the optical absorption coefficient of the epidermis, the optical absorption coefficient $\mu_2$ indicates the optical absorption coefficient of the dermis, and the optical absorption coefficient $\mu_3$ indicates the optical absorption coefficient of the subcutaneous tissue.

$$\begin{cases} \int_0^\tau \ln\left(\frac{N'(t)}{I'(t)}\right) L_1(t) dt = \sum_{i=1}^3 \mu_i \int_0^\tau L_1(t) L_i(t) dt \\ \int_0^\tau \ln\left(\frac{N'(t)}{I'(t)}\right) L_2(t) dt = \sum_{i=1}^3 \mu_i \int_0^\tau L_2(t) L_i(t) dt \\ \int_0^\tau \ln\left(\frac{N'(t)}{I'(t)}\right) L_3(t) dt = \sum_{i=1}^3 \mu_i \int_0^\tau L_3(t) L_i(t) dt \end{cases} \quad (15)$$

where $N'(t) = \dfrac{N(t)}{N_{in}}$ and $I'(t) = \dfrac{I(t)}{I_{in}}$

Here, ln(A) denotes a natural logarithm of A, and N(t) denotes a light intensity at a time t in a model of a time-resolved waveform of short-pulsed light of a specific wavelength $\lambda_k$. $I_{in}$ denotes a light intensity of the short-pulsed light irradiated by the irradiation unit 304. $N_{in}$ denotes the number of photons according to irradiation in a simulation performed by the simulation unit 301.

When the optical absorption coefficient calculation unit 310 calculates the optical absorption coefficients $\mu_1$ to $\mu_3$ of the layers of the skin in a certain integral interval, the optical absorption coefficient distribution storage unit 311 stores the optical absorption coefficients $\mu_1$ to $\mu_3$ of the layers of the skin in the certain integral interval calculated by the optical absorption coefficient calculation unit 310 (step S56).

When the optical absorption coefficient calculating unit 310 calculates the optical absorption coefficients $\mu_1$ to $\mu_3$ of the layers of the skin in the certain integral interval, the optical absorption coefficient calculation unit 310 determines whether or not optical absorption coefficients of the dermis in the set integral interval have been calculated (step S57).

In this embodiment, because a blood sugar level is measured by designating the main components of the skin as four types of water, protein, lipid, and glucose, the optical absorption coefficient calculation unit 310 determines whether or not the optical absorption coefficients $\mu_1$ to $\mu_3$ for four types of wavelengths $\lambda_1$ to $\lambda_4$ have been calculated. Here, the wavelengths $\lambda_1$ to $\lambda_4$ are selected from among a plurality of wavelengths for which the simulation unit 301 has calculated optical path length distributions and time-resolved waveforms.

Here, if the optical absorption coefficient calculation unit 310 determines that there is an uncalculated optical absorption coefficient among the optical absorption coefficients $\mu_1$ to $\mu_3$ of the dermis in the set integral interval (step S57: NO), the process returns to step S52 of acquiring received light intensities at certain times, the uncalculated optical absorption coefficients of the dermis are calculated, and the determination (step S57) as to whether or not the optical absorption coefficients of the dermis in the set integral interval have been calculated is re-performed.

On the other hand, if the optical absorption coefficient calculation unit 310 determines that the optical absorption coefficients $\mu_1$ to $\mu_3$ of the dermis in the set integral interval have been calculated (step S57: YES), an optical absorption coefficient is acquired from the optical absorption coefficient distribution of the dermis (step S58).

The optical absorption coefficient acquisition unit 312 determines whether or not optical absorption coefficients of which the number is the number of wavelengths corresponding to the number of types of main components of the skin have been calculated (step S44).

Here, if the optical absorption coefficient acquisition unit 312 determines that the optical absorption coefficients of which the number of wavelengths corresponding to the number of types of main components of the skin have not been calculated (step S44: NO), the process returns to step S41 of irradiating short-pulsed light, an uncalculated optical absorption coefficient of which the number of wavelengths corresponding to the number of types of main components of the skin is calculated, and the determination (step S44) as to whether or not the optical absorption coefficients have been calculated is re-performed.

On the other hand, if the optical absorption coefficient acquisition unit 312 determines that the optical absorption coefficients of which the number is the number of wavelengths corresponding to the number of types of main components of the skin have been calculated (step S44: YES), the concentration calculation unit 313 calculates a concentration of glucose included in the dermis based on the above-described Equations (14) (step S45).

According to this embodiment as described above, the optical absorption coefficients $\mu_1$ to $\mu_3$ are calculated by an integration value of optical path lengths for the time $\tau$. Thereby, it is possible to reduce the influence on calculation results of the absorption coefficients $\mu_1$ to $\mu_3$ due to an error included in measured light intensities I(t).

Sixth Embodiment

Figure 18:
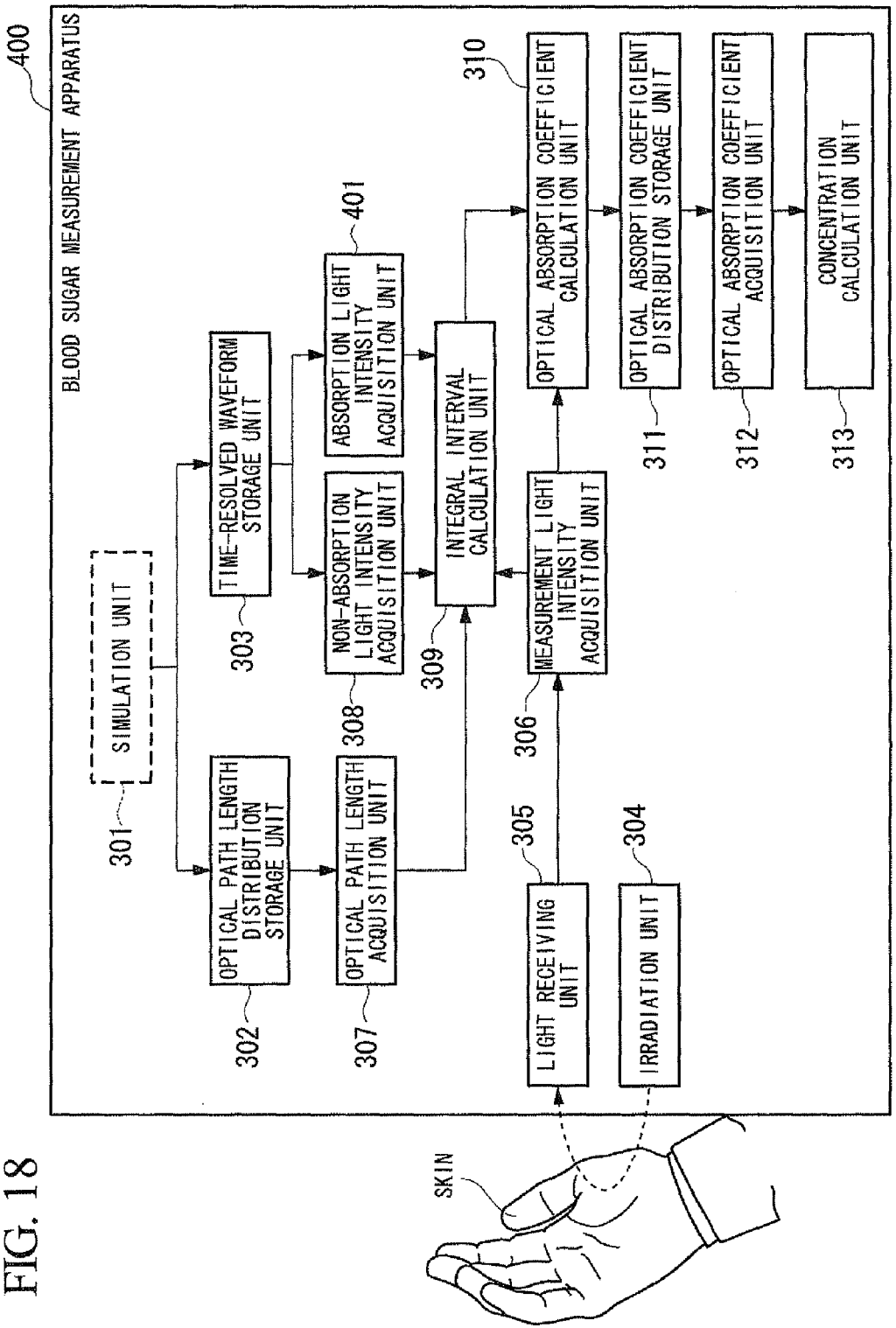
FIG. 18 is a schematic block diagram showing a configuration of a blood sugar measurement apparatus (a concentration determination apparatus) in accordance with a sixth embodiment of the present invention.

FIG. 18 is a schematic block diagram showing a configuration of a blood sugar measurement apparatus (a concentration determination apparatus) in accordance with a sixth embodiment of the present invention.

A difference of a blood sugar measurement apparatus 400 of this embodiment from the blood sugar measurement apparatus 300 of the fourth embodiment is that an absorption light intensity acquisition unit (a light intensity model acquisition unit) 401 is provided in parallel to the non-absorption light intensity acquisition unit 308 between the time-resolved waveform storage unit 303 and the integral interval calculation unit 309.

The absorption light intensity acquisition unit 401 acquires a light intensity model when an optical absorption coefficient at a certain time like a non-absorption light intensity obtained by the simulation unit 301 is 1, that is, upon 100% absorption.

Here, an absorption light intensity at a predetermined time of a model of a time-resolved waveform of short-pulsed light, that is, an absorption light intensity at a certain time, is acquired from the time-resolved waveform storage unit 303 storing the absorption light intensity.

The integral interval calculation unit 309 calculates an integral interval of an area corresponding to a light intensity of a specific layer from a light intensity distribution, based on an optical path length of each layer of the skin of a model of an optical path length distribution acquired by the optical path length acquisition unit 307, a non-absorption light intensity of a model of a time-resolved waveform of short-pulsed light acquired by the non-absorption light intensity acquisition unit 308, an absorption light intensity of the model of the time-resolved waveform of the short-pulsed light acquired by the absorption light intensity acquisition unit 401, and the light intensity distribution of light received by the light receiving unit 305 acquired by the measurement light intensity acquisition unit 306.

If a blood sugar level is measured using the blood sugar measurement apparatus 400, an optical absorption coefficient of the dermis is calculated by varying the integral interval.

In this case, the integral interval calculation unit 309 calculates an integral interval by use of (1) a time from when a light intensity output by the light receiving unit 305 receiving backscattered light is detected at more than minimum detection sensitivity of the measurement light intensity acquisition unit 306 to when a light intensity equal to the minimum detection sensitivity is detected, (2) a time characteristic of a non-absorption light intensity acquired from the time-resolved waveform storage unit 303 storing the non-absorption light intensity obtained by the simulation unit 301, (3) a time characteristic of an absorption light intensity acquired from the time-resolved waveform storage unit 303 storing the absorption light intensity obtained by the simulation unit 301, (4) a distance between the light receiving unit 305 and the irradiation unit 304 in contact with a skin surface, and (5) the size and optical characteristics (such as a scattering coefficient, an absorption coefficient, an anisotropy parameter, or a refractive index) of a skin model provided to the simulation unit 301. More specifically, a start time, an end time, and an increment time of the integral interval are calculated.

Because a method and procedure in which a concentration of glucose included in a layer of a specific depth is calculated by the optical absorption coefficient calculation unit 310 to the concentration calculation unit 313 based on the integral interval calculated by the integral interval calculation unit 309 are the same as those of the blood sugar measurement apparatus 300 of the fourth embodiment, descriptions thereof are omitted here.

In this embodiment, like the fourth embodiment, it is also possible to select an optical absorption coefficient of the dermis in a combination close to an optical path length distribution of a skin structure. Therefore, it is possible to accurately measure an optical absorption amount of the glucose, that is, a glucose concentration, in the dermis of the skin, and consequently, it is possible to non-invasively and accurately determine the glucose concentration in the dermis.

Also, it is possible to improve an accuracy of measurement of a concentration of glucose in the dermis by varying the integral interval.

While preferred embodiments of the present invention have been described and illustrated above, it should be understood that these are examples of the present invention and are not to be considered as limiting. Additions, omissions, substitutions, and other modifications can be made without departing from the scope of the present invention.

For example, although the ease where a concentration of glucose included in a dermis of skin is measured by taking a blood sugar measurement apparatus as a concentration determination apparatus, skin as an observed object, glucose as a target component, and short-pulsed light as pulse light has been described in the above-described embodiments, the present invention is not limited thereto. The concentration determination method may be used in other apparatuses for determining a concentration of a target component in a specific layer of an observed object formed of a plurality of light scattering medium layers. Short-pulsed light of a specific wavelength may be replaced with continuous light of a specific wavelength.

For example, the present invention may be effectively used to inspect, diagnose, or medically treat skin disease if the present invention is applied to a portable concentration measurement apparatus for main components of the skin.

What is claimed is:

1. A concentration determination apparatus that determines a concentration of a target component in a specific layer of an observed object formed of a plurality of layers, the concentration determination apparatus comprising:

a memory storing:
  a model of an optical path length distribution in each layer of the plurality of layers of the observed object from a short-pulsed light irradiated at the observed object, and
  a model of a time-resolved waveform; and
an irradiation device configured to irradiate short-pulsed light at the observed object;
a light receiving device configured to receive light backscattered from the observed object by the irradiation of the short-pulsed light;
a processor programmed to:
  acquire an intensity distribution of the light based on an intensity of the light received by the light receiving device;
  acquire the optical path length distribution of each layer of the plurality of layers at a predetermined time based on the stored model of the optical path length distribution;
  acquire a light intensity model at a predetermined time based on the stored model of the time-resolved waveform;
  calculate a integral interval of an area corresponding to a light intensity distribution of the specific layer from the intensity distribution of the light based on the intensity distribution of the light, the optical path length distribution, and the light intensity model;
  acquire light intensities at a plurality of times $t_1$ to $t_m$ when the number of layers of the observed object within the integral interval is equal to or greater than n;
  calculate an optical absorption coefficient of the target component in the specific layer by varying the integral interval for a combination of the intensity distribution of the light and the plurality of layers of the acquired model of the time-resolved waveform, the optical absorption coefficient being calculated based on:

$$\begin{cases} N(t_1)\ln\left(\dfrac{N(t_1)}{I(t_1)}\right) = \sum_{i=1}^{n} \mu_i L_i(t_1) \\ \vdots \\ N(t_m)\ln\left(\dfrac{N(t_m)}{I(t_m)}\right) = \sum_{i=1}^{n} \mu_i L_i(t_m); \end{cases} \quad (1)$$

acquire the optical absorption coefficient of the target component in the specific layer based on the calculated optical absorption coefficient of each layer of the plurality of layers; and
  calculate the concentration of the target component in the specific layer based on the acquired optical absorption coefficient of the target component, wherein
$\ln(\bullet)$ denotes a natural logarithm, $I(t)$ denotes a light intensity received by the light receiving device at a time t within the integral interval, $N(t)$ denotes a light intensity at the time t within the integral interval of the model of the time-resolved waveform of the short-pulsed light, $L_i(t)$ denotes an optical path length of an i-th layer at the time t within the integral interval of the model of the optical path length distribution, and $\mu_i$ denotes an optical absorption coefficient of the i-th layer; and
the integral interval includes an integral over time period t corresponding to the light intensity distribution of the specific layer.

2. The concentration determination apparatus according to claim 1, wherein the processor includes:
  acquiring a non-absorption light intensity model among light intensity models of the short-pulsed light stored in the memory; and
  acquiring an absorption light intensity model among the light intensity models of the short-pulsed light stored in the memory.

3. The concentration determination apparatus according to claim 1, wherein the plurality of times at which the light intensities are acquired include a peak time of an optical path length distribution of each layer of the plurality of layers.

4. The concentration determination apparatus according to claim 1, wherein
the processor is programmed to:
  acquire light intensities for at least a predetermined time $\tau$ from a predetermined time within the integral interval, and
  calculate an optical absorption coefficient of the specific layer from:

$$\begin{cases} \int_0^\tau \ln\left(\dfrac{N(t)}{I(t)}\right) L_1(t)\, dt = \sum_{i=1}^{n} \mu_i \int_0^\tau L_1(t) L_i(t)\, dt \\ \vdots \\ \int_0^\tau \ln\left(\dfrac{N(t)}{I(t)}\right) L_n(t)\, dt = \sum_{i=1}^{n} \mu_i \int_0^\tau L_n(t) L_i(t)\, dt \end{cases} \quad (2)$$

where $\ln(\bullet)$ denotes a natural logarithm, $I(t)$ denotes a light intensity received by the light receiving device at a time t within the integral interval, $N(t)$ denotes a light intensity at the time t within the integral interval of the model of the time-resolved waveform of the short-pulsed light, $L_i(t)$ denotes an optical path length of an i-th layer at the time t within the integral interval of the model of the optical path length distribution, n denotes the number of layers of the observed object, and $\mu_i$ denotes an optical absorption coefficient of the i-th layer.

5. The concentration determination apparatus according to claim 1, wherein
the irradiation device irradiates light of a plurality of wavelengths 1 to q, and
processor is programmed to:
  calculate the optical absorption coefficient in the specific layer for each of the plurality of wavelengths irradiated by the irradiation device, and
  calculate the concentration of the target component in the specific layer from:

$$\begin{cases} \mu_{a(1)} - \mu_{a(2)} = \sum_{j=1}^{p} g_j(\varepsilon_{j(1)} - \varepsilon_{j(2)}) \\ \vdots \\ \mu_{a(q-1)} - \mu_{a(q)} = \sum_{j=1}^{p} g_j(\varepsilon_{j(q-1)} - \varepsilon_{j(q)}) \end{cases} \quad (3)$$

where $\mu_{a(i)}$ denotes an optical absorption coefficient of a wavelength i in an a-th layer, which is the specific layer, $g_j$ denotes a molar concentration of a j-th component forming the observed object, $\varepsilon_{j(i)}$ denotes an optical absorption coefficient of the wavelength i of the j-th component, p denotes the number of main components forming the observed object, and q denotes the number of types of wavelengths irradiated by the irradiation device.

6. The concentration determination apparatus according to claim 5, wherein a plurality of pieces of light irradiated by the irradiation device include light of a wavelength at which the optical absorption coefficient of the target component becomes large.

7. The concentration determination apparatus according to claim 5, wherein a plurality of pieces of light irradiated by the irradiation device include light of a wavelength at which orthogonality of an absorption spectrum distribution of each component of main components constituting the observed object becomes high.

8. A concentration determination method using a concentration determination apparatus having a processor for determining a concentration of a target component in a specific layer of an observed object formed of a plurality of layers, the concentration determination apparatus including a memory configured to store: (i) a model of an optical path length distribution in each layer of the plurality of layers from short-pulsed light irradiated at the observed object, and (ii) a model of a time-resolved waveform of the short-pulsed light irradiated at the observed object, the concentration determination method comprising:

irradiating, by an irradiation device, the short-pulsed light to the observed object;

receiving, by a light receiving device, light backscattered from the observed object by the irradiation of the short-pulsed light;

acquiring, by the processor of the concentration determination apparatus, an intensity of the light received by the light receiving device;

acquiring, by the processor of the concentration determination apparatus, the optical path length distribution of each layer of the plurality of layers at a predetermined time based on the stored model of the optical path length distribution;

acquiring, by the processor of the concentration determination apparatus, a light intensity model at the predetermined time of the stored model of the time-resolved waveform of the short-pulsed light;

calculating, by the processor of the concentration determination apparatus, a integral interval of an area corresponding to a light intensity distribution of the specific layer from the intensity distribution of the light based on the intensity distribution of the light, the acquired optical path length distribution of each layer of the plurality of layers, and the acquired light intensity model;

acquiring light intensities at a plurality of times $t_1$ to $t_m$ when the number of layers of the observed object within the integral interval is equal to or greater than n;

calculating, by the processor of the concentration determination apparatus, an optical absorption coefficient of the target component in the specific layer by varying the calculated integral interval for a combination of the acquired intensity distribution of the light and a plurality of models of the acquired time-resolved waveform, the optical absorption coefficient being calculated based on:

$$\begin{cases} N(t_1)\ln\left(\frac{N(t_1)}{I(t_1)}\right) = \sum_{i=1}^{n} \mu_i L_i(t_1) \\ \vdots \\ N(t_m)\ln\left(\frac{N(t_m)}{I(t_m)}\right) = \sum_{i=1}^{n} \mu_i L_i(t_m); \end{cases} \quad (1)$$

acquiring the optical absorption coefficient of the target component in the specific layer based on the calculated optical absorption coefficient of each layer of the plurality of layers; and calculating, by the processor, the concentration of the target component in the specific layer based on the acquired optical absorption coefficient of the target component t, wherein ln(•) denotes a natural logarithm, I(t) denotes a light intensity received by the light receiving device at a time t within the integral interval, N(t) denotes a light intensity at the time t within the integral interval of the model of the time-resolved waveform of the short-pulsed light, $L_i(t)$ denotes an optical path length of an i-th layer at the time t within the integral interval the model of the optical path length distribution, and $\mu_i$ denotes an optical absorption coefficient of the i-th layer; and the integral interval includes an integral over time period t corresponding to the light intensity distribution of the specific layer.

9. A non-transitory computer-readable medium storing a program for use with a processor of a concentration determination apparatus for determining a concentration of a target component in a specific layer of an observed object, wherein the concentration determination apparatus includes a memory configured to store: (i) a model of an optical path length distribution in each layer of a plurality of layers from short-pulsed light irradiated to the observed object formed of the plurality of layers, and (ii) a model of a time-resolved waveform of the short-pulsed light irradiated to the observed object, the program causing the processor to execute:

an irradiation procedure of irradiating the short-pulsed light to the observed object;

a light receiving procedure of receiving light backscattered from the observed object by the irradiation of the short-pulsed light;

a light intensity acquisition procedure of acquiring an intensity of the light received in the light receiving procedure;

an optical path length acquisition procedure of acquiring the optical path length distribution of each layer of the plurality of layers at a predetermined time of the model of the optical path length distribution from the memory;

a light intensity model acquisition procedure of acquiring a light intensity model at the predetermined time of the model of the time-resolved waveform of the short-pulsed light from the memory;

an integral interval calculation procedure of calculating a integral interval of an area corresponding to a light intensity distribution of the specific layer from the intensity distribution of the light based on the intensity distribution of the light acquired in the light intensity acquisition procedure, the optical path length distribution of each layer of the plurality of layers acquired in the optical path length acquisition procedure, and the light intensity model acquired in the light intensity model acquisition procedure;

a light intensity acquisition procedure of acquiring light intensities at a plurality of times $t_1$ to $t_m$ when the number of layers of the observed object within the integral interval is equal to or greater than n;

an optical absorption coefficient calculation procedure of calculating an optical absorption coefficient of the target component in the specific layer by varying the integral interval calculated in the integral interval calculation procedure for a combination of the intensity distribution of the light acquired in the light intensity acquisition procedure and a plurality of models of the time-resolved waveform acquired in the light intensity model acquisition procedure the optical absorption coefficient being calculated based on:

$$\begin{cases} N(t_1)\ln\left(\dfrac{N(t_1)}{I(t_1)}\right) = \sum_{i=1}^{n} \mu_i L_i(t_1) \\ \quad\vdots \\ N(t_m)\ln\left(\dfrac{N(t_m)}{I(t_m)}\right) = \sum_{i=1}^{n} \mu_i L_i(t_m); \end{cases} \quad (1)$$

an optical absorption coefficient acquisition procedure of acquiring the optical absorption coefficient of the target component in the specific layer based on the calculated optical absorption coefficient of each layer of the plurality of layers; and a concentration calculation procedure of calculating the concentration of the target component in the specific layer based on the optical absorption coefficient of the target component acquired in the optical absorption coefficient calculation and acquisition procedure, wherein $\ln(\bullet)$ denotes a natural logarithm, $I(t)$ denotes a light intensity received by the light receiving device at a time t within the integral interval, $N(t)$ denotes a light intensity at the time t within the integral interval of the model of the time-resolved waveform of the short-pulsed light, $L_i(t)$ denotes an optical path length of an i-th layer at the time t within the integral interval of the model of the optical path length distribution, and $\mu_i$ denotes an optical absorption coefficient of the i-th layer; and the integral interval includes an integral over time period t corresponding to the light intensity distribution of the specific layer.

* * * * *